(12) United States Patent
Hu et al.

(10) Patent No.: US 11,532,109 B2
(45) Date of Patent: Dec. 20, 2022

(54) PROPERTY BASED IMAGE MODULATION FOR FORMATION VISUALIZATION

(71) Applicant: HALLIBURTON ENERGY SERVICES, INC., Houston, TX (US)

(72) Inventors: Yangqiu Hu, Houston, TX (US); Naum Derzhi, Houston, TX (US); Jonas Toelke, Houston, TX (US)

(73) Assignee: HALLIBURTON ENERGY SERVICES, INC., Houston, TX (US)

( * ) Notice: Subject to any disclaimer, the term of this patent is extended or adjusted under 35 U.S.C. 154(b) by 0 days.

(21) Appl. No.: 17/059,557

(22) PCT Filed: Jan. 24, 2020

(86) PCT No.: PCT/US2020/014905
§ 371 (c)(1),
(2) Date: Nov. 30, 2020

(87) PCT Pub. No.: WO2021/150237
PCT Pub. Date: Jul. 29, 2021

(65) Prior Publication Data
US 2021/0407156 A1    Dec. 30, 2021

(51) Int. Cl.
*G06T 11/20*    (2006.01)
*G06T 11/00*    (2006.01)
(Continued)

(52) U.S. Cl.
CPC .......... *G06T 11/206* (2013.01); *E21B 47/002* (2020.05); *E21B 49/00* (2013.01);
(Continued)

(58) Field of Classification Search
CPC .......... E21B 44/00; E21B 45/00; E21B 49/00; E21B 21/08; E21B 44/02; E21B 41/00;
(Continued)

(56) References Cited

U.S. PATENT DOCUMENTS

| 6,125,203 A | 9/2000 | Keskes et al. |
| 7,366,616 B2 | 4/2008 | Bennett et al. |

(Continued)

FOREIGN PATENT DOCUMENTS

CN    106934760 A    7/2017

OTHER PUBLICATIONS

English abstract of CN106934760; retrieved from www.espacenet.com on Jan. 23, 2020.

(Continued)

*Primary Examiner* — Todd Buttram
(74) *Attorney, Agent, or Firm* — Novak Druce Carroll LLP

(57) ABSTRACT

A graphical representation of an image of a subterranean formation along with log properties of the formation provided in a single graphical representation. Logged formation property values are coded into graphic representations of images of the formation in order to provide a graphical representation which allows the user to visually perceive the formation images and the logged formation properties simultaneously. A method may include receiving an image of a formation, the image including image values based on the formation, and also receiving a log property of the formation, the log property including log property values based on the formation. The log property values of the formation are correlated to corresponding locations in the image. A transfer function with the image values and the correlated log property values as inputs is determined. Based on the transfer function, a joint graphical representation of the image and the log property is rendered.

17 Claims, 12 Drawing Sheets

(51) Int. Cl.
    *E21B 47/002* (2012.01)
    *E21B 49/00* (2006.01)
    *G01N 33/24* (2006.01)

(52) U.S. Cl.
    CPC ............ *G01N 33/24* (2013.01); *G06T 11/001* (2013.01); *G06T 2200/04* (2013.01); *G06T 2210/62* (2013.01)

(58) Field of Classification Search
    CPC .......... E21B 47/022; E21B 7/00; E21B 10/00; E21B 25/00; E21B 41/0092; E21B 44/04; E21B 47/00; E21B 47/002; E21B 47/10; E21B 10/43; E21B 37/00; E21B 49/003; E21B 10/26; E21B 10/42; E21B 21/01; E21B 43/00; E21B 43/2406; E21B 44/06; E21B 47/0002; E21B 47/003; E21B 47/04; E21B 47/06; E21B 49/005; E21B 49/06; E21B 49/10; E21B 7/04; E21B 7/06; E21B 7/10; E21B 12/02; E21B 47/0003; E21B 47/065; E21B 47/07; E21B 47/1025; E21B 47/117; G06T 17/05; G06T 11/206; G06T 11/001; G06T 11/203; G06T 11/60; G06T 17/00; G06T 17/20; G06T 19/20; G06T 2219/2021; G06T 7/0085; G06T 7/0097; G06T 7/13; G06T 7/174; G01V 1/301; G01V 2210/66; G01V 1/345; G01V 2210/643; G01V 99/005; G01V 1/302; G01V 1/32; G01V 1/34; G01V 2210/641; G01V 8/02; G01V 1/30; G01V 2210/64; G01V 3/38; G01V 11/002; G01V 1/306; G01V 1/40; G01V 1/50; G01V 2210/48; G01V 2210/63; G01V 2210/644; G01V 2210/65; G01V 3/083; G01V 3/12; G01V 3/32; G01V 99/00; G01V 11/00; G01V 1/003; G01V 1/305; G01V 2210/74; E21C 39/00; G01C 19/02; G01N 24/081; G01R 33/4828; G01R 33/561; G01R 33/5611; G01R 33/5617; G05B 15/02; G06F 17/10; G06F 17/00; G06F 17/50; G06F 2111/10; G06F 30/00; G06F 30/20; G06Q 10/06; G06Q 10/06312; G09G 2340/14; G09G 5/02; H04N 1/60; H04N 5/33; H04N 5/23206; H04N 5/23299; H04N 5/77; H04N 9/735; A61P 9/00; B60J 3/0208; Y02A 90/30

See application file for complete search history.

(56) References Cited

U.S. PATENT DOCUMENTS

| | | | |
|---|---|---|---|
| 8,908,964 | B2 | 12/2014 | Tin |
| 9,135,888 | B2 | 9/2015 | McClanahan |
| 2007/0239359 | A1 | 10/2007 | Stelting et al. |
| 2015/0279093 | A1* | 10/2015 | Sung ...................... G06T 17/05 345/420 |
| 2017/0205531 | A1* | 7/2017 | Berard ...................... E21B 7/04 |
| 2017/0254920 | A1 | 9/2017 | Appel et al. |
| 2017/0285211 | A1* | 10/2017 | Monteiro ............... B82Y 30/00 |
| 2019/0195061 | A1 | 6/2019 | Ramsay et al. |
| 2019/0257161 | A1* | 8/2019 | Dewald ................... E21B 19/07 |
| 2020/0302678 | A1* | 9/2020 | Miao ....................... G01V 3/26 |

OTHER PUBLICATIONS

International Search Report, Response and Written Opinion, PCT Application No. PCT/US2020/014905, dated Oct. 7, 2020.

* cited by examiner

Depth

PROPERTY BASED IMAGE MODULATION FOR FORMATION VISUALIZATION

CROSS-REFERENCE TO RELATED APPLICATIONS

This application is a national stage entry of PCT/US2020/014905 filed Jan. 24, 2020, said application is expressly incorporated herein by reference in its entirety.

FIELD

The present disclosure relates to the visualization and display of formation sample images. In particular, the present disclosure relates to graphical representation of formations, and in particular graphically representing associated images and properties.

BACKGROUND

Subterranean rock formations and their associated properties are investigated for a variety of purposes including planning and development of wellbore sites, including drilling, production, and fracturing. One way to evaluate subterranean formations involves extracting samples of the formations, for example, extracting them from a wellbore during or after drilling. These formation samples can be analyzed in a laboratory setting to evaluate various properties of the geologic formations present throughout the length of the wellbore. In addition to extracting samples, evaluation of the rock formations may be performed using formation measurements performed inside the wellbore, directly on the formation.

Analysis of the rock formation and of samples thereof may encompass a number of methods, including imaging and logging of properties of the samples and formations. Images of the samples may represent two dimensional (2-D) and/or three dimensional (3-D) spatial distributions of a property of the formation sample. Formation images can also be obtained inside the wellbore directly on the formation. The visual analysis of the images may provide information regarding the texture of the rock sample. Images of the formations and samples can be processed (such as via processor of FIG. 13) to obtain values of additional properties, which are also represented as formation and sample property images. Images can also be processed to identify surfaces separating distinct parts or components of the formation.

Properties of the sample and formation may also be logged. The logged (or log) properties are evaluated along a single dimension (1-D) of the formation sample or depth dimension of the well bore. The images as well as the logged properties may be visually evaluated in order to determine aspects of the formation. However, the images and formation properties are often presented graphically in different ways. As a result, when visually evaluating the obtained data, users often are required to shift focus between the image renderings on the one hand, and log property displays on the other.

BRIEF DESCRIPTION OF THE DRAWINGS

In order to describe the manner in which the advantages and features of the disclosure can be obtained, reference is made to embodiments thereof which are illustrated in the appended drawings. Understanding that these drawings depict only exemplary embodiments of the disclosure and are not therefore to be considered to be limiting of its scope, the principles herein are described and explained with additional specificity and detail through the use of the accompanying drawings in which.

DETAILED DESCRIPTION

Various embodiments of the disclosure are discussed in detail below. While specific implementations are discussed, it should be understood that this is done for illustration purposes only. A person skilled in the relevant art will recognize that other components and configurations may be used without parting from the spirit and scope of the disclosure.

The present disclosure is directed to methods and systems for the analysis of downhole formation samples by graphically representing images of the formation samples along with log properties of the formation in a single graphic. In particular, methods and systems disclosed herein involve encoding logged formation property values into graphic representations of images of the formation in order to provide a graphical representation which allows the user to visually perceive the formation images and the logged formation properties simultaneously. The present method improves the processing system for graphically depicting image and corresponding properties for visualization by a user.

Figure 1A:
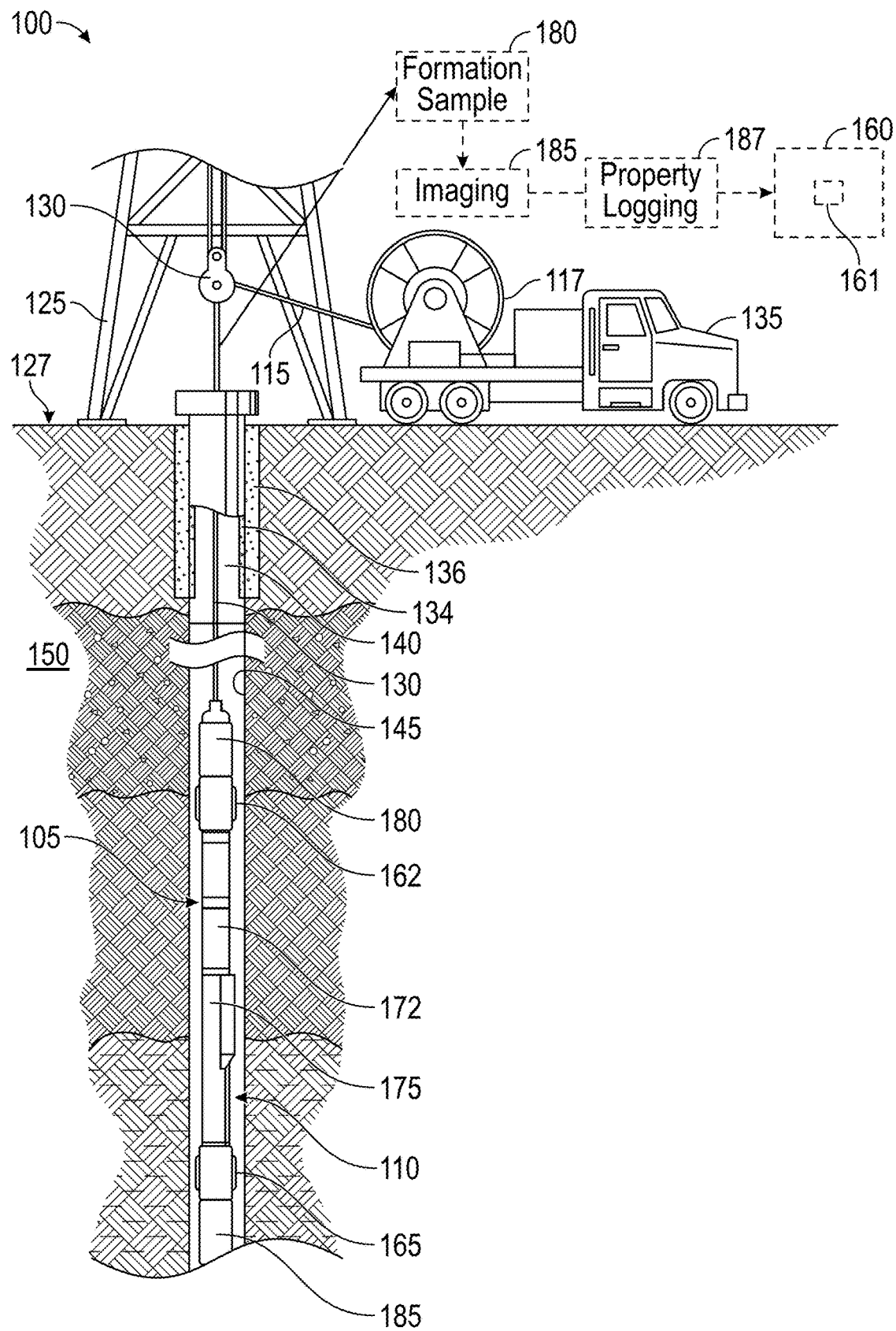
FIG. 1A is a schematic view of a wellbore operating environment in which a formation sample may be obtained, according to various aspects of the present disclosure.

FIG. 1A illustrates a schematic view of an embodiment of a wellbore operating environment 100 extending through a subterranean formation from which a formation sample, also referred to as a core, may be extracted from a sidewall of the wellbore. As depicted, the operating environment 100 includes a derrick 125 that supports a hoist 130 at the surface 127. Here it is assumed that a drill string has been removed from a wellbore 110 to allow a downhole core sampling apparatus 105 to be lowered into the wellbore 110 that has been previously drilled through one or more formations 150. As depicted, downhole core sampling apparatus 105 can be lowered into wellbore 110 by conveyance 115 coupled with hoist 130 drawn from spool 117. As shown, a casing 134 has been previously secured within the wellbore 110 by cement 136. The conveyance 115 can be anchored to the derrick 125 or portable or mobile units such as a truck 135. As depicted in FIG. 1A, the downhole core sampling apparatus 105 is lowered into wellbore 110 penetrating one or more formations 150 to a desired core sampling zone after which the downhole core sampling apparatus 105 may sample cores from the sidewall 145 of wellbore 110. The core sampling apparatus 105 can include an elongate housing 110, a first sealing element 162, a second sealing element 165, a sidewall coring tool 172, a core storage assembly 175.

While FIG. 1A depicts a first sealing element 162 and a second sealing element 165, a downhole core sampling apparatus 105 that includes only a single sealing element is within the spirit and scope of the present disclosure. Upon sealing engagement by the first sealing element 162, a second sealing element 165, the sidewall coring tool 170 may drill into or otherwise extract a formation sample from the sidewall of the wellbore 140. The sidewall formation sample 180 may be brought to the surface 117 and subject to imaging 185, as well as formation property logging 187. The formation sample obtained may be any suitable length for testing or extraction, including about ½ inch (1.27 cm) to about 5 inches (12.7 cm), or alternatively from about 1 inch (2.54 cm) to about 4 inches (10.16 cm), or alternatively from about 1.5 inches (3.81 cm) to about 2.5 inch (6.35 cm) in length. These formation samples may be from about 1.5 to about 4 inches in diameter, or alternatively from about 2 inches to about 3 inches, or alternatively from about 2 to about 2.4 inches in diameter. The formation imaging 185 and/or property logging 187 may be carried out offsite in a laboratory. Processing center 160 may be employed for processing images, property logging and/or rendering graphics or carrying out other processing as disclosed herein and may include one or more processors 161 for such purpose. For instance, the processing center 160 may be an on-site or off-site laboratory for analyzing image properties and log properties of the formation samples.

Figure 1B:
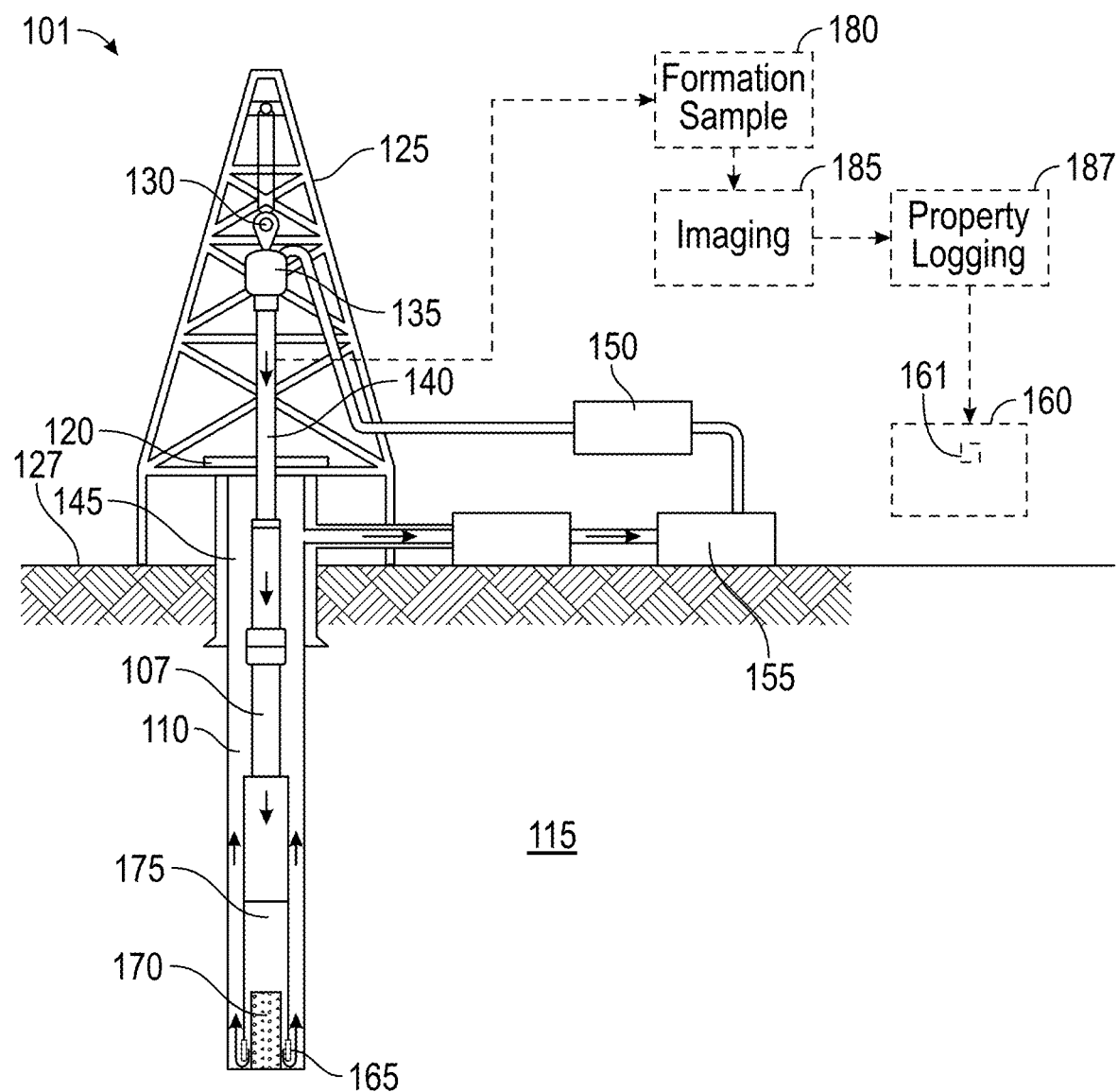
FIG. 1B is a schematic view of a wellbore operating environment in which formation samples (sidewall cores) can be obtained, according to various aspects of the present disclosure.

FIG. 1B illustrates an exemplary environment 101 in which a formation sample, also referred to as a core, may be extracted from a subterranean formation. The wellbore drilling environment 100 illustrates a drill string 107 extending in a wellbore 110 of a formation 150. The drill string 155 extends from a platform 120. As depicted in FIG. 1, along with platform 120 is a derrick 125 that supports a hoist 130 for raising and lowering a drill string 107. A swivel 135 is provided from which a Kelly 140 extends suitable for rotating and lowering the drill string 107 through the well entrance 145. A pump 150 pumps a drilling fluid in the direction shown by the arrows through the drill string and then up through an annulus of the wellbore 110 and to the mud tank or pit 155. The processor 160 having one or more processors 161 may be provided for control of the drilling and/or analyzing samples. Sample analysis may be conducted in a laboratory on site or remotely and maybe employed for processing imaging, property logging and/or rendering graphics or carrying out other processing as disclosed herein.

Figure 12:
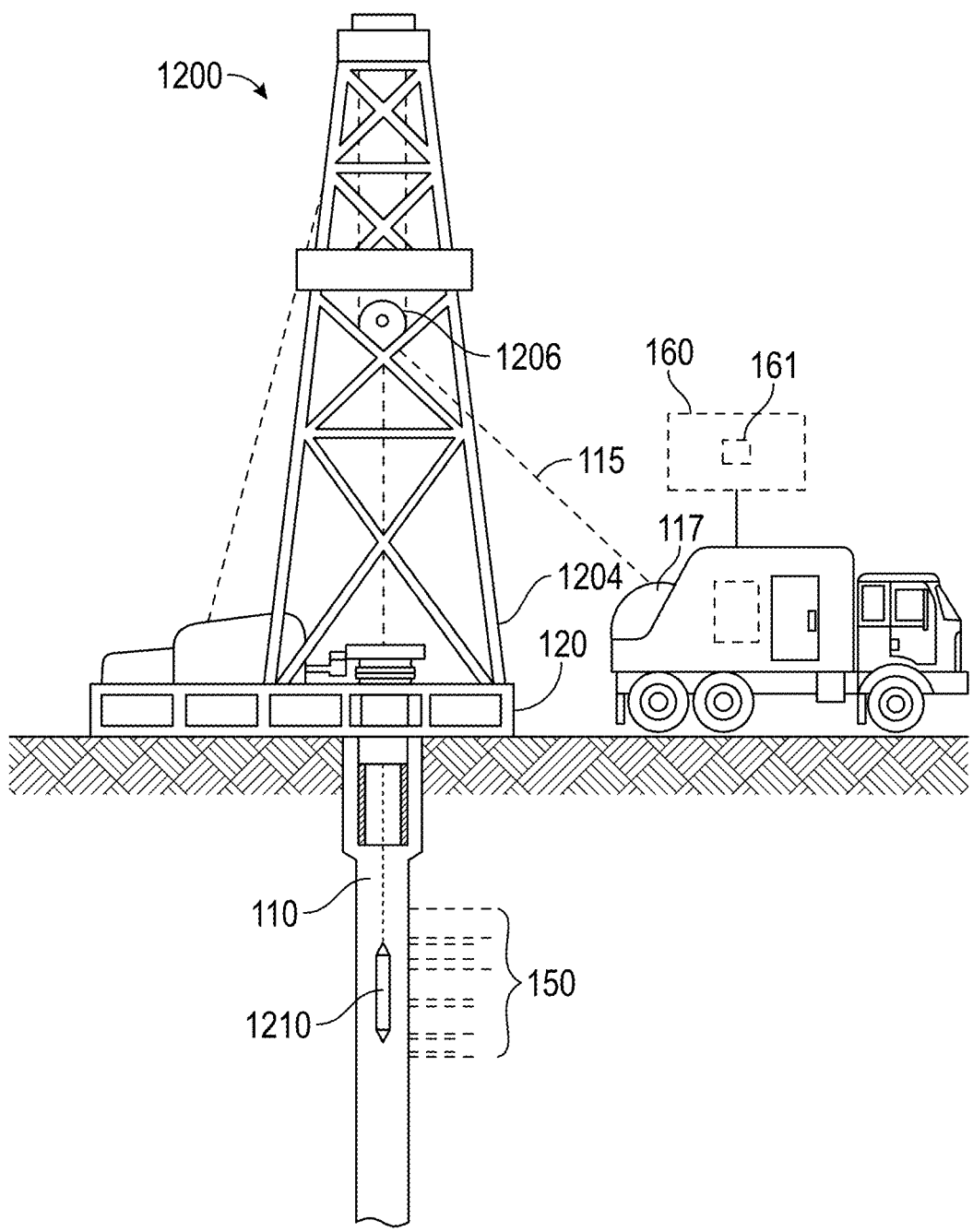
FIG. 12 is a schematic view of a wellbore operating environment in which formation property values can be obtained, according to various aspects of the present disclosure.

The drill string 107 has a hollowed drill bit 165 which has a hollow center or portion for receiving a formation sample 170. The drill string 107 may include a core chamber 175 for retaining the formation sample until it is brought to the surface. The formation sample 170 may be any suitable length for testing or extraction, including about ½ inch (1.27 cm) to about 5 inches (12.7 cm), or alternatively from about 1 inch (2.54 cm) to about 4 inches (10.16 cm), or alternatively from about 1.5 inches (3.81 cm) to about 2.5 inch (6.35 cm) in length. The formation samples may also be longer and may be less than 1 foot, or from 1 foot to 3 to 5 feet, or alternatively from 5 to 50 feet, or alternatively from 5 to 100 feet, or as much as 500 feet long. Longer samples may be cut into smaller samples of 1 to 4 feet for analysis. The extracted formation sample 170 may be in a cylindrical shape due to the shape in which it is cut by the drill bit 165 and retained. The drill string 107 may incorporate components for logging while drilling (LWD) or measurement while drilling (MWD) which may measure various properties or carrying out imaging of the formation which may be communicated to the surface via wire, or wirelessly, such as by acoustic transmission or mud pulse telemetry. In this way, in addition to obtaining a formation sample during drilling, imaging and or log properties can be obtained during drilling. Alternatively, or additionally, the drill string 105 may be removed and wireline logging tools (as shown in FIG. 12) may be provided within the wellbore 110 to measure and log various properties of the formation 115, to obtain well bore images, and to extract formation samples from the walls of the well bore.

While FIGS. 1A and 1B illustrate ways of obtaining a formation sample (also referred to as cores in the field), the manner of obtaining a formation sample is not limited, and may be obtained in any method. For instance, while drill bit 165 includes a hollow center, conventional drill bits may be employed, and formation cuttings and pieces of the formation obtained from conventional drilling may be used as samples.

Accordingly, formation samples may be obtained via sidewall core extraction as shown in FIG. 1A, or via a hollow drill bit as in FIG. 1B. The formation samples may be referred to as cores, and may include but are not limited to whole core, sidewall core, slabbed core, plugs, cuttings, formation fragments, and the like. The formation samples extracted from the well bore or obtained in any other way can be iteratively subdivided into a smaller samples (subsamples). The term formation sample encompasses both the whole sample, subsamples, portions of the sample and fragments. The term formation sample herein may also include formation components that are not extracted but which remain within the wellbore but have been imaged or analyzed for its properties.

In order to evaluate the formation samples, imaging of the samples may be carried out. For instance, as shown in FIG. 1B, a formation sample 180, which may be the formation sample 180 or a portion thereof, may be subject to imaging 185 with an imaging device. The formation sample 180 may also be evaluated for formation properties via property logging 187 which may then be further processed in processing center 160 having one or more processors 161. As mentioned, the imaging 185 and property logging 187 of the sample may be carried out offsite in a laboratory or elsewhere, and associated graphical rendering are discussed in more detail below.

The imaging may provide information regarding the physical structure, texture, and spatial distribution of properties of the formation sample or the well bore. While the human eye cannot see through the formation sample structure, the imaging device may use methods which interrogate and/or detect throughout the interior portion of the formation sample to generate image data. An imaging device may be employed to inspect the formation sample and obtain the desired images. The image obtained depends on the particular property interrogated and/or detected. Exemplary imaging includes for instance, computerized tomography (CT). CT employs x-ray attenuation measurements which may involve an x-ray source that produces x-rays which may be absorbed by the formation sample, and where x-rays exiting from the formation sample are sensed by detectors. The signals produced by detectors are recorded. Signals produced at numerous angles of orientation of the core with respect to the source-detectors system are collected and processed to collectively form a 3-D image of the formation sample. The use of CT herein is only one exemplary imaging technique, as any imaging technique maybe used including any x-ray imaging, magnetic resonance imaging (MRI), scanning electron microscopy (SEM), electrical imaging, resistivity, optical imaging, and acoustical imaging. Imaging as disclosed herein may include a two-dimensional imaging (such as white-lite, UV-light, X-Ray projection, or thin section photography and the like), a three-dimensional imaging (such as a computerized tomography (CT), scanning electron microscopy (SEM)), MRI, or any other method or device suitable for evaluating 2-D or 3-D distribution of a property within the sample.

The image of a formation represents a 2-D or 3-D distribution of a property, such as X-Ray attenuation, electrical conductivity, density, PE and similar, of this formation. The image may be represented in numeric form, such as an ordered collection of values of the imaged property. The image property values represent a function of two or three spatial coordinates $v(x_1, x_2, x_3)$, where v is the value of the property at location determined by values of two or three spatial coordinates $x_1, x_2, x_3$, which can be determined in any spatial coordinate system.

The image properties obtained may be continuous or categorical. The continuous properties are those for which any value within certain limits defined by physical considerations is valid. For example, any value of formation density from 0 and 15 g/cc can be considered valid. The value of the property in this case would be continuous from 0 to 15. Other continuous properties include resistivity, porosity, PE, etc. which may similarly be presented in a range between limits. Some properties may not have an upper or lower limit. In addition to, or alternative to continuous properties, the properties evaluated within the sample or wellbore can be categorical, or discrete, properties. Categorical properties can include, but are not limited to, facies, facies subtypes, formations, rock types, rock subtypes, petro-physical rock types, electro-facies, and clusters thereof. The types of categorical properties can be consistent throughout certain depth ranges of the earth formations, and therefore these sections can be evaluated together. The formation sample may be divided according to these categorical properties. While continuous properties are values within a range of values, categorical properties are a singular value indicating a type or category. The singular value may be chosen from a plurality of singular values, depending on the property, each indicating a type or a category. For instance designation of formation types can be considered as a categorical formation property, having discrete values. Each type of formation sample rock may be designated a corresponding value. Accordingly, the number of available categories corresponds to the number of formation rock types. Categorical properties can be determined at numerous depth points of interest throughout a wellbore or at different locations within the formation samples, and this determination may be based on historical knowledge of formation types or newly obtained by using or combining the geologic a priori knowledge and select measured formation properties taken both via samples in the laboratory and directly within the wellbore.

The image may be rendered into a graphical representation. The graphical representation of the image may be visually evaluated by a user to gain information and make conclusions about the formation sample. Visual evaluation may allow qualitative analysis and conclusions, such as rock type or texture, or other information which can be gained by the visual perception of user viewing the graphical representation of the image.

The graphical representation can be a 2-D or 3-D distribution of visual elements, whose characteristics, such as color, brightness, and the like, are related to the image property values $v(x_1, x_2, x_3)$. The transfer function defines the relationship between the property value of the image and its contribution to the characteristics of the visual element of the graphical representation, which this value is affecting. As such, this transfer function is a function of one independent variable, namely the image property value $v(x_1, x_2, x_3)$. Since the visual element of the graphical representation has one or more characteristics, expressed by one or more numeric values, the transfer function may have one or more components.

The characteristics of the visual element of the graphical representation of an images can be collectively called its color. The color can be defined in any suitable color space including, but not limited to, red, green, blue (RGB); hue, saturation, value (HSV); CIE (including CIE 1931 XYZ, C1E1976 L*, u*, v* (CIELUV), CIE LAB, and CIEUVW); cyan, magenta, yellow, and key (CMYK) color model; luma plus chroma/chromiance (including YIQ, YUV, YDbDr, YPbPr, YCbCr, ICtCp, and xvYCC); cylindrical transformations including HSV, HSL, CIELCHab and CIELChuv); and grayscale color spaces. Thus the transfer function defines relationship between the value of the image property and each of the components of any of these color spaces, and may be implemented as a multi-component function of one variable.

Even when the image data acquired is 3-D, it still may be presented, displayed or otherwise visualized on a flat screen or other canvas, i.e. on a 2-D surface. Accordingly, the graphical representation, and the encoding transfer function may provide for a 3-D representation on the 2-D surface. When rendering a 3-D image into a 2-D or 3-D graphic representation it may be necessary to assign a transparency or opacity value to each location of the image. The relationship between the opacity value and the image value is also a part of the transfer function, becoming an additional component of the transfer function.

A transfer function can be represented as a multi-component function $F_i$ of a single variable $v(x_1, x_2, x_3)$, i.e., the following function $$F_i[v(x_1,x_2,x_3)] \qquad (1)$$

where i enumerates the components of the color space and opacity, v is a value of the formation image at a location with coordinates $(x_1,x_2,x_3)$.

Figures 2A, 2B, 2C:
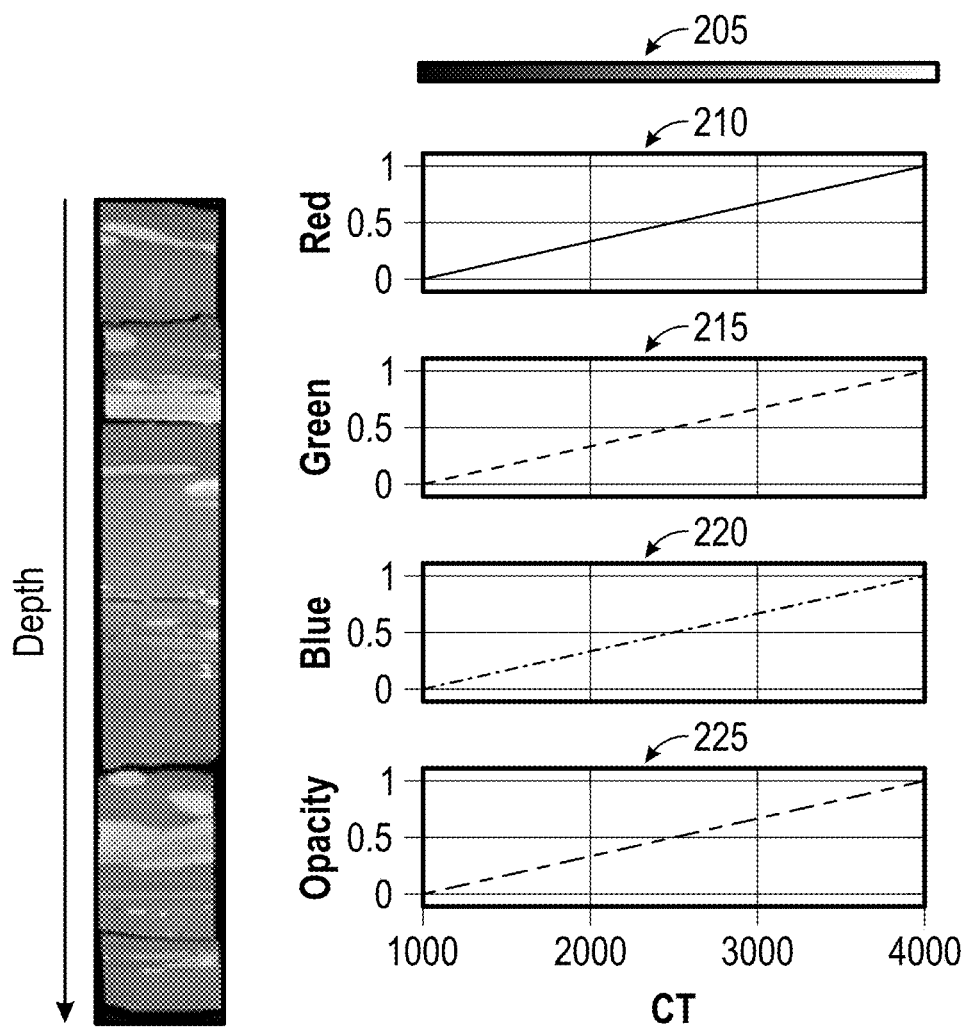
FIG. 2A illustrates an exemplary graphical representation of a 2-D cross-section of a 3-D CT image of a rock sample (in this case a whole core) rendered with the use of a gray-scale transfer function, according to various aspects of the present disclosure.
FIG. 2B depicts charts illustrating the relationship between red, green and blue components of a gray-scale transfer function expressed in RGB space transfer function on the one hand, and the image property value (CT) on the other hand, according to various aspects of the present disclosure.
FIG. 2C illustrates the a graphical rendering of an image with opacity to depict a 3-D image as a 2-D projection, according to various aspects of the present disclosure.

FIG. 2A illustrates an exemplary graphical representation of a 2-D cross-section of a 3-D CT image of a rock sample (in this case a whole core) rendered with the use of a gray-scale transfer function expressed in RGB space, where all color components of the transfer function have the same value for a given value of the argument v. FIG. 2B illustrates the relationship between red 210, green 215 and blue 220 components of this transfer function on the one hand, and the property value (CT) on the other hand. Further, gray-scale legend 205 illustrates how the property value (in this case, CT) defines the color of the graphic element corresponding to this value. In this case increase in CT value corresponds to increase in the visual intensity of the graphical representation. Visual analysis of the graphical representation in FIG. 2A reveals differences in the texture of the image along its depth, providing evidence of the geologic history of the formation. In particular, it reveals that the rock sample has inclusions, which are 3-D in shape, for which a 2-D cross section does not provide an adequate representation.

To better analyze the 3-D shapes present in the sample the 3-D image may be rendered as 2-D projection, rather than a 2-D cross-section, with the addition of opacity component of the transfer function. FIG. 2B illustrates an example CT-Opacity component 225, showing an opacity relationship to property (CT) value, which makes volume elements with higher property (CT) values more opaque, and therefore showing through elements with lower property values. The FIG. 2C illustrates the result of such rendering, with orthogonal projection of the 3-D volume parallel to its Y axis. It shows additional image features missed by the 2-D cross section. A significant advantage of such rendering is the opportunity it provides to vary the direction of the projection, which reveals the spatial relationship between image features in 3 dimensions. Every component of the gray-scale transfer function illustrated in FIG. 2B can be expressed as the same linear function of the formation property value:

$$F_i=(v-\text{scaleMin})/(\text{scaleMax}-\text{scaleMin}) \qquad (2)$$

where scaleMin and scaleMax define the property scaling.

Figures 3A, 3B, 3C:
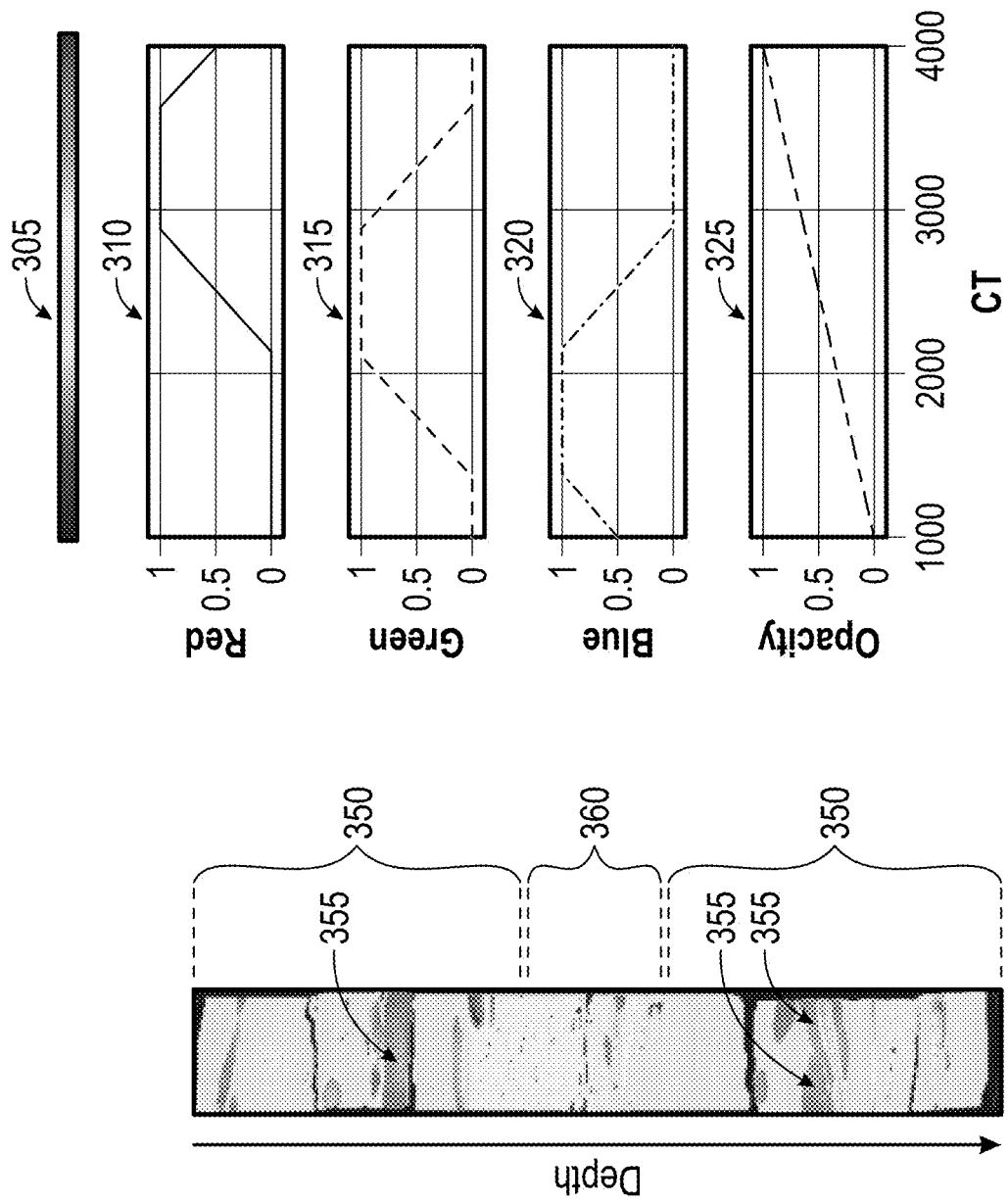
FIG. 3A illustrates an exemplary graphical representation of a 2-D cross-section of a 3-D CT image of a rock sample (in this case a whole core) rendered with the use of a color transfer function, according to various aspects of the present disclosure.
FIG. 3B depicts charts illustrating the relationship between red, green and blue components of this transfer function on the one hand, and the image property value (CT) on the other hand, according to various aspects of the present disclosure.
FIG. 3C illustrates the a color graphical rendering of an image with opacity to depict a 3-D image as a 2-D projection, according to various aspects of the present disclosure.

The color components' relationships to property value may differ from each other in any number of ways, and may be of arbitrary form. FIGS. 3A and 3C illustrate renderings similar to those in FIGS. 2A and 2C, but in this implementation instead of gray-scale transfer function a color transfer function is used, resulting in "false color" graphic representations. FIG. 3B illustrates the relationship between red 310, green 315, and blue 320 components of this transfer function on the one hand, and the property value (CT) on the other hand. The color legend 305 illustrates how the property value, in this case CT, defines a change in the visible color from violet/blue on the left side of the color legend 305 to orange/red on the right side, with green to yellow in the middle. The benefit of false color representation is illustrated, in particular, in the different texture which the color revealed in the middle of the sample of FIG. 3A, and which was not apparent in the gray-scale representation. FIG. 3B illustrates an example CT-opacity component 325, showing a opacity relationship to property (CT) value, which makes volume elements with higher property (CT) values more opaque, with FIG. 3C illustrating the result of such rendering as compared to FIG. 3A without such rendering. In FIG. 3A and FIG. 3C, the colors are provided corresponding to the colors and opacity in FIG. 3B, with areas 350 showing greenish color and area 360 showing yellowish color, and patches 355 showing reddish/orange color.

Transfer functions may be implemented as lookup tables. In such implementation a transfer function is represented by a suitable number of rows, with columns corresponding to the transfer function component. For each image location the transfer function row index used to render the property value at that location is selected based on the image value. This may be done, for example, by linearly mapping the property value to the row index. In case of categorical image properties the value of the property may be directly used as row index.

In addition, or alternatively, the formation properties may be evaluated with logging tools at various depth locations in the well bore. Formation properties values can be acquired with acoustic measurements, electromagnetic measurements or other logging tools. Specifically, subterranean formation properties including, but not limited to, bulk density, photoelectrical factor (PE), porosity, fluid saturation and composition, permeability and other fluid flow characteristics, mineral composition, elastic and geo-mechanical properties, and various other properties may be evaluated using logging tools.

In addition to imaging, additional analysis of the formation samples is carried out regarding the formation properties, referred to herein as log properties. Whereas the image data provide 2-D or 3-D spatial distribution of a certain formation sample property, the same and other formation log properties are evaluated at various locations along a single dimension of the formation sample. The property evaluation may be performed by physical measurement of property values in the laboratory setting or at the well site. Such properties include, but are not limited to, weight fractions of chemical elements using X-ray fluorescence (XRF), spectral gamma ray counts, mineral composition using X-ray diffraction (XRD), porosity, absolute and relative permeability, density, pore and pore throat size distributions, and many other properties routinely evaluated by means of routine and special core analysis.

In addition, or alternatively, the sample property images can be used for quantitative evaluation of formation properties. These include, but are not limited to, bulk density, porosity, PE, mineral fractions distribution, absolute and relative permeability, pore and pore throat size distributions, grain size characteristics, conductivity, elasticity and other properties by utilizing the methods of digital rock analysis known to the person of ordinary skill.

The values of formation log property obtained in physical measurements on the sample or from sample images, may characterize the sample as a whole. They also may be obtained in several locations along the sample, thus characterizing the property distribution along the sample. The property values obtained on the sample can be correlated to the locations within the wellbore using the knowledge of the well bore depth from which the sample had been extracted. Conversely, the formation properties measured directly in the wellbore, i.e. "log properties," can be correlated to locations within the formation sample. Such log properties can be obtained in a laboratory after extracting a formation sample as in FIGS. 1A and 1B, or of the formation from within a wellbore as described below with respect to FIG. 12.

The log formation properties obtained may be continuous or categorical, which are defined the same as image properties above.

The formation log properties evaluated at locations along a single dimension, whether along the depth dimension of the well bore, or along a single dimension of the formation sample, are collectively referred to as log properties. These log properties are necessary to make decisions concerning the field operations related to this and other wells. In order to make the decisions concerning the field operations, the log properties may be rendered into a graphical representation, illustrating the property values variations with depth or another dimension.

Figure 4B:
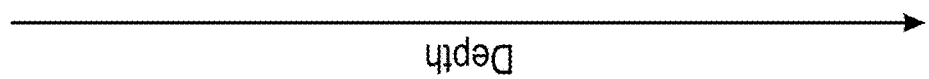
FIG. 4B is an exemplary graphical representation of a categorical log property, according to various aspects of the present disclosure.
Figure 4B:
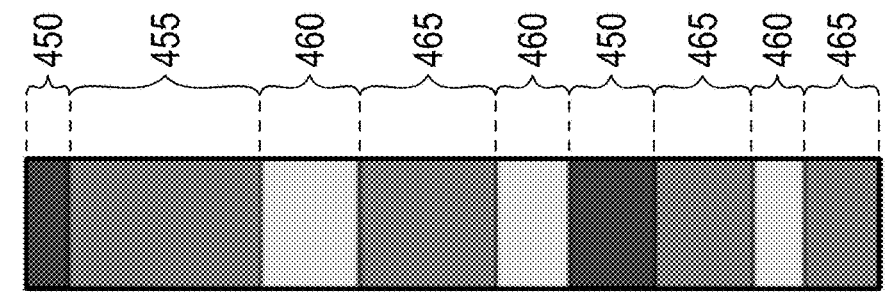
Figure 4A:
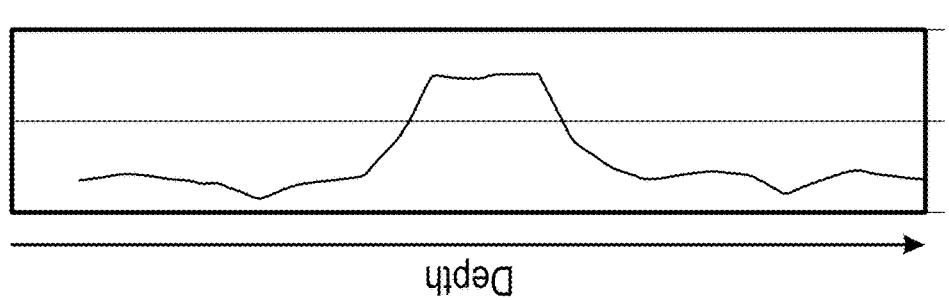
FIG. 4A is an exemplary graphical representation of a continuous log property ("Total gamma" in this example, which is total intensity of the gamma ray radiation of the formation) evaluated along the wellbore or the formation sample, according to various aspects of the present disclosure.

FIG. 4A is an exemplary graphical representation of a continuous log property "Tot. gamma," which is total intensity of the gamma ray radiation of the formation evaluated along the wellbore via a conveyance tool or of a formation sample in a laboratory, and expressed in API units. In this example the values of this property are plotted in a log track as a function of the formation depth. The locations where the log curve deviates to the right (the figure being provided on a sheet with FIG. 4A on the left side of the sheet and FIG. 5D on the right side) from the middle of the track are those with higher gamma ray radiation, which may indicate increased concentration of clay minerals. These locations may be interpreted as belonging to shale lithology. While Tot. gamma is employed in this example, any other log properties obtained as described above may be employed, including those listed herein, with interpretation of their values specific to each kind of property and known to persons of ordinary skill in the art. FIG. 4B is an exemplary graphical representation of a categorical log property, which, in this example, represents rock type evaluated along the wellbore or the formation sample. Different categorical values are graphically represented as different colors, and therefore locations with different colors are interpreted as different rock types, while locations with the same color indicate the same formation rock type at these locations. As an example, FIG. 4B graphically represents blue segments as 450, gray segments as 455, green segments as 460 and red segments as 465. Any other categorical log property may be represented in similar ways, with meaning of different colors defined specifically by each property.

Figure 5D:
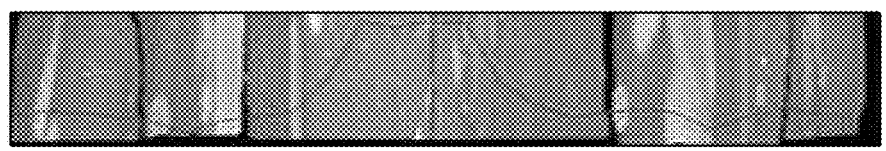
FIG. 5D is an exemplary combination of graphical representation of the 2-D image cross-section overlaid with the graphical representation of the continuous property log, according to various aspects of the present disclosure.
Figure 5C:
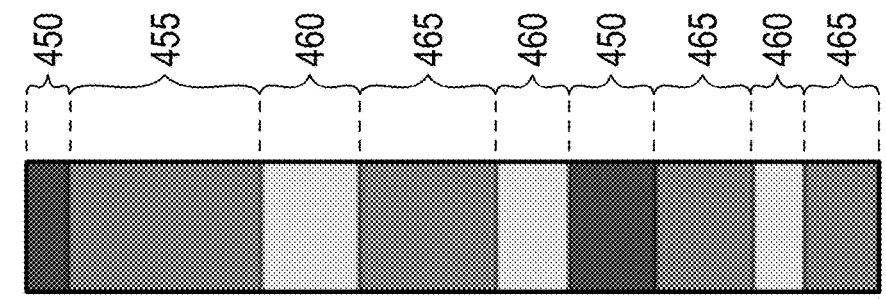
FIG. 5C is an exemplary graphical representation of a categorical property, according to various aspects of the present disclosure.
Figure 5B:
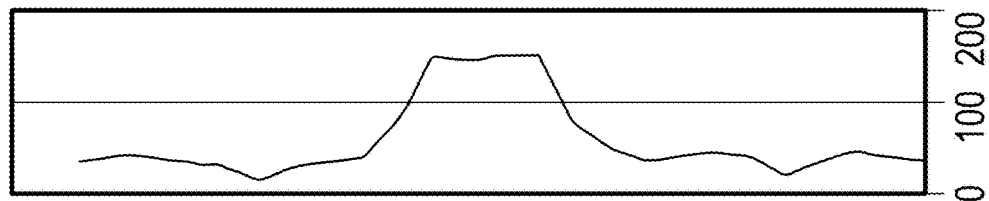
FIG. 5B is an exemplary graphical representation of a continuous property, according to various aspects of the present disclosure.
Figure 5A:
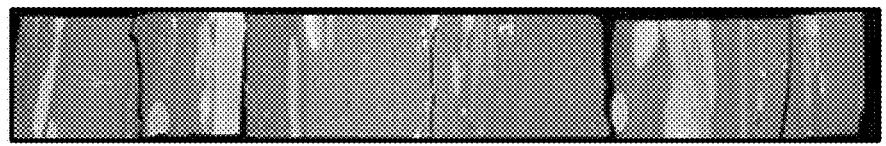
FIG. 5A illustrates a graphical representation of a 2-D cross-section of a 3-D image of formation property (CT), according to various aspects of the present disclosure.

It is advantageous to visually analyze the formation property images and formation log property values together. FIGS. 5A-5D illustrate an exemplary conventional dual graphical representation of the formation image along with graphical representations of continuous and categorical log properties. FIG. 5A illustrates a graphical representation of a 2-D cross-section of a 3-D distribution of formation property (CT). FIG. 5B is an exemplary graphical representation of a continuous property. FIG. 5C is an exemplary graphical representation of a categorical property; and FIG. 5D is an exemplary combination of graphical representation of the 2-D image cross-section overlaid with the graphical representation of the continuous log property. Placing representations of the image and log property in close proximity, like in these examples, makes their dual perception and interpretation easier. However, the difference in the representation modes of these data, where the image is represented by the changes in the intensity and/or color, while the log property is represented by the change in the curve shape, still do not allow to perceive both types of data in the same way.

The current disclosure disclosed methods for joined graphic representation of formation images and log properties, enhancing the ease of their joint interpretation by encoding both data sets into their joint graphic representation using a modified definition of the transfer function. Accordingly, rather than just simply overlaying a curve, the modified transfer function jointly renders the data set into a graphical representation, thereby improving the underlying processing and improving the user's perception of the data and experience in evaluation.

The modification consists of at least one component of the transfer function to become dependent upon at least two inputs: the value of the image property in a given image location, and the value of the log property at the location correlated with the said image location. This modification is applicable to both continuous and categorical formation log properties.

The modified transfer function can be expressed as $$F_i[v(x_1,x_2,x_3),u(y)] \quad (3)$$

where i enumerates the components of the color space and opacity, v is the value of formation property image at the location with coordinates $(x_1,x_2,x_3)$, u is the value of the formation log property at the location with coordinate y correlated with location $(x_1,x_2,x_3)$ of the image. In this way the values of the formation log property u modulate the parameters of the transfer function and of the graphical representation.

Figure 6A:
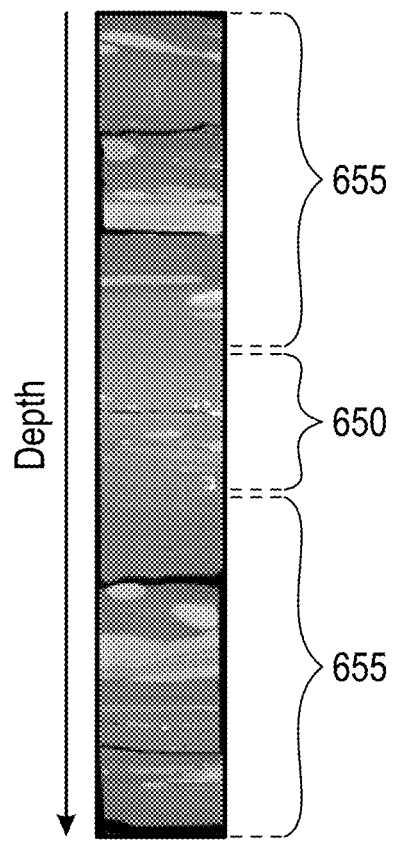
FIG. 6A illustrates an exemplary graphical representation of the 2-D cross section of a CT image, of a whole core, illustrated in FIG. 2A, rendered with the modified transfer function.
Figure 6B:
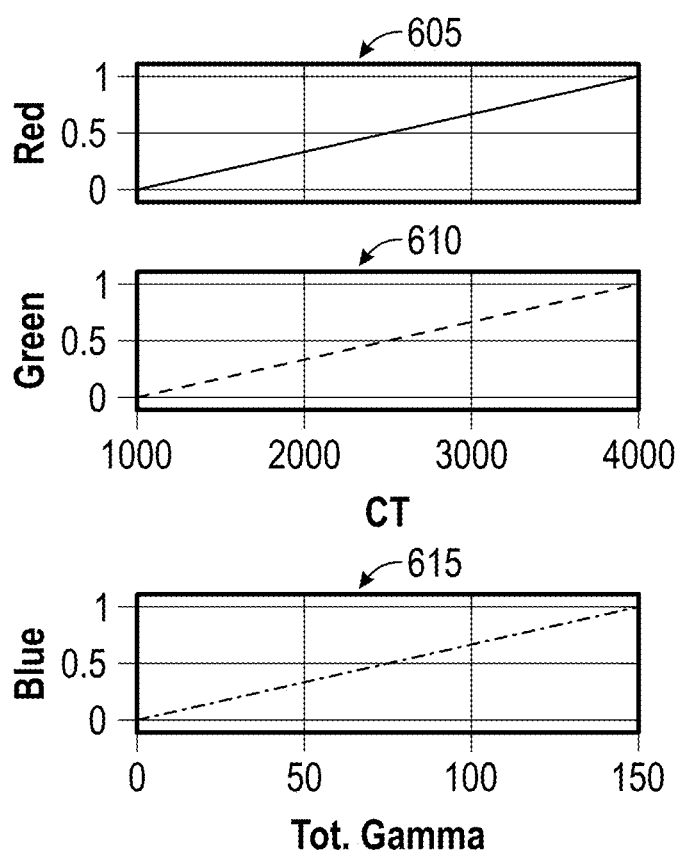
FIG. 6B depict charts having red and green components respectively, in linear relationship with the CT property value, while the blue component is in linear relationship with the log property (total gamma) value, according to various aspects of the present disclosure.

FIG. 6A illustrates an exemplary graphical representation of the 2-D cross section of a CT image, of a whole core, illustrated in FIG. 2A, rendered with the modified transfer function, modulated by continuous log property (such as total gamma) values, illustrated in FIG. 4A. In this example the locations of the rock sample correlated to the depth of higher total gamma values show shades of blue color in section 650, while the locations correlated to lower total gamma values show shades of yellow color, such as in sections 655. In this way the user perceived simultaneously the increase in intensity of total gamma ray and the changes in the core texture, which makes the joint interpretation of the data easier. In this example the red and green components of the RGB color-space transfer function, illustrated in FIG. 6B are red 605 and green 610 components respectively, in linear relationship with the CT property value, while the blue 615 component is in linear relationship with the total gamma value, with additional condition that the blue component is zero where CT is 0, thus making this component an explicit function of two variables.

In the functional form, the modified transfer function used in this example can be expressed as follows:

$$R = (CT - 1000)/(4000 - 1000)$$
$$G = (CT - 1000)/(4000 - 1000)$$
$$B = \frac{\text{Gamma}}{150}; B(CT = 0) = 0$$

Where R, G, and B are values of the RGB color-space transfer function components, CT is the value of the formation sample CT image property and Gamma is the value of total gamma formation log property.

Though these examples illustrate the application of the method to formation sample images, the method can be applied in exactly the same way to the well bore images.

Figure 7A:
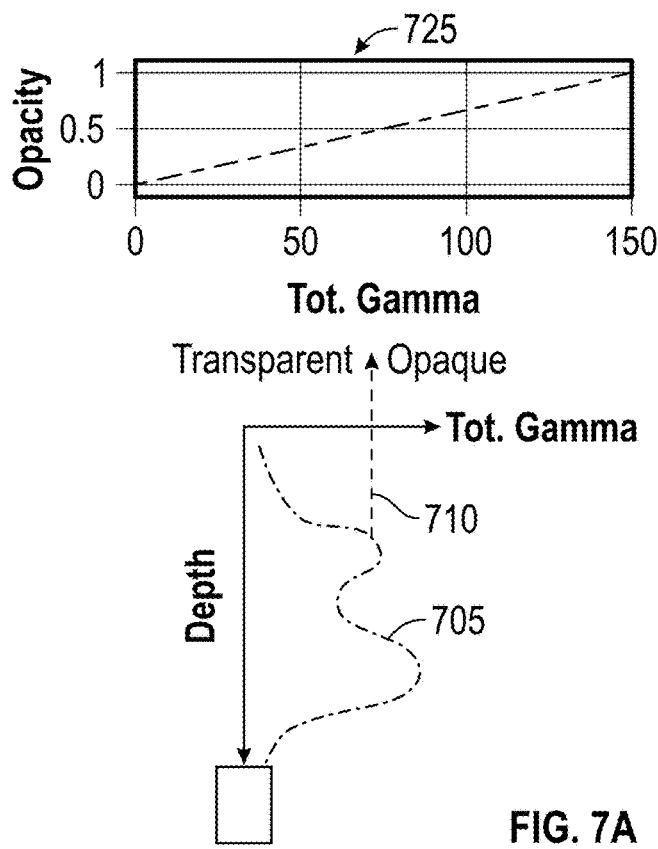
FIG. 7A illustrates an exemplary opacity transfer function modulation for a continuous property, thereby mapping a log formation property to opacity, according to various aspects of the present disclosure.
Figure 7B:
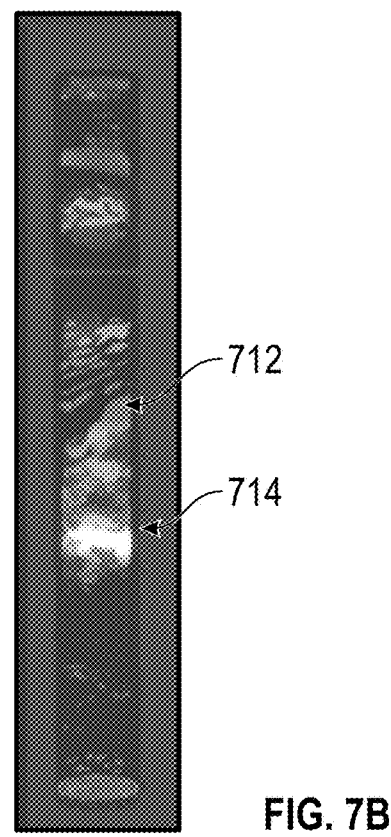
FIG. 7B illustrates simultaneous display of the image and its formation properties, according to various aspects of the present disclosure.

The opacity component may be modulated in similar way. FIG. 7A illustrates an exemplary opacity transfer function modulation for a continuous log property, thereby mapping a log formation property to opacity. For instance, FIG. 7A illustrates a graph 705 of a log formation property, such as Tot. gamma values as a function of depth. The graph 705 is comparable to the graph shown in FIG. 4A in that both are showing a formation property, in this case Tot. gamma. Although Tot. Gamma is shown, any log formation property may be equivalently used. An arrow 710 points from the curve to an opacity graph 725 showing opacity increasing from the left side of the figure to the right side of the figure, namely from most transparent to completely opaque. Each Tot. gamma value corresponds to a particular opacity in the legend. Therefore, an example point in curve 705, which is a particular value, points a particular opacity value in the opacity graph as shown by the arrow. Accordingly, a graphical representation of an image, such as that in FIG. 2A or 5A, may be modulated to have the opacity based on the formation property measurements such as from FIG. 4A, and/or shown for instance in graph 705 of 7A, mapping the log property value to opacity according to FIG. 7A. As a result, the previous graphical rendering of a formation sample image, such as in FIG. 2A or 5A may be overlaid with the log formation property in FIG. 7A, such that the image is modulated according to the mapping shown in FIG. 7A, resulting in the simultaneous display of the image and log properties as shown in FIG. 7B on a computer screen or other canvas. A user may therefore upon viewing the graphical rendering simultaneously perceive the value of the property, such as the Tot. gamma, and the structure of the sample as represented by the image.

Accordingly, FIG. 7B illustrates a graphical representation of an image of a formation sample modified with an opacity transfer function modulation. The transfer function for rendering the graphical representation is modulated according to a selected transfer function such as that in FIG. 7A, to show the Tot. gamma log property of FIG. 4A in terms of opacity represented in FIG. 7A. Consequently, FIG. 7B appears to a user as though the image of the formation sample is overlaid with the corresponding formation property, but displayed in terms of opacity with such display being on a computer screen or other canvas. For instance, area 712 is shown with low opacity thereby illustrating a low value of Tot gamma, whereas, the area 714 is shown with high opacity, thereby illustrating a high value of Tot. gamma.

In the functional form, the modified transfer function used in this example can be expressed as follows:

$$R = (CT - 1000)/(4000 - 1000)$$
$$G = (CT - 1000)/(4000 - 1000)$$
$$B = (CT - 1000)/(4000 - 1000)$$
$$\text{Opacity} = \frac{\text{Gamma}}{150}; \text{Opacity}(CT = 0) = 0$$

Where R, G, and B are values of the RGB color-space transfer function components, Opacity is the value of the opacity component, CT is the value of the formation sample CT image property and Gamma is the value of total gamma formation log property.

The categorical log properties may be used for modulating the transfer function parameters in the same way as continuous properties. In addition, or alternatively, the values of the categorical properties, being integer in their nature, may be used as indices into a look up table of a set of transfer functions, each of which is a traditional transfer function, depending only upon the image property value. In this way gray-scale transfer function may be used for one rock type, and false-color transfer function may be used for another rock type.

Figure 8:
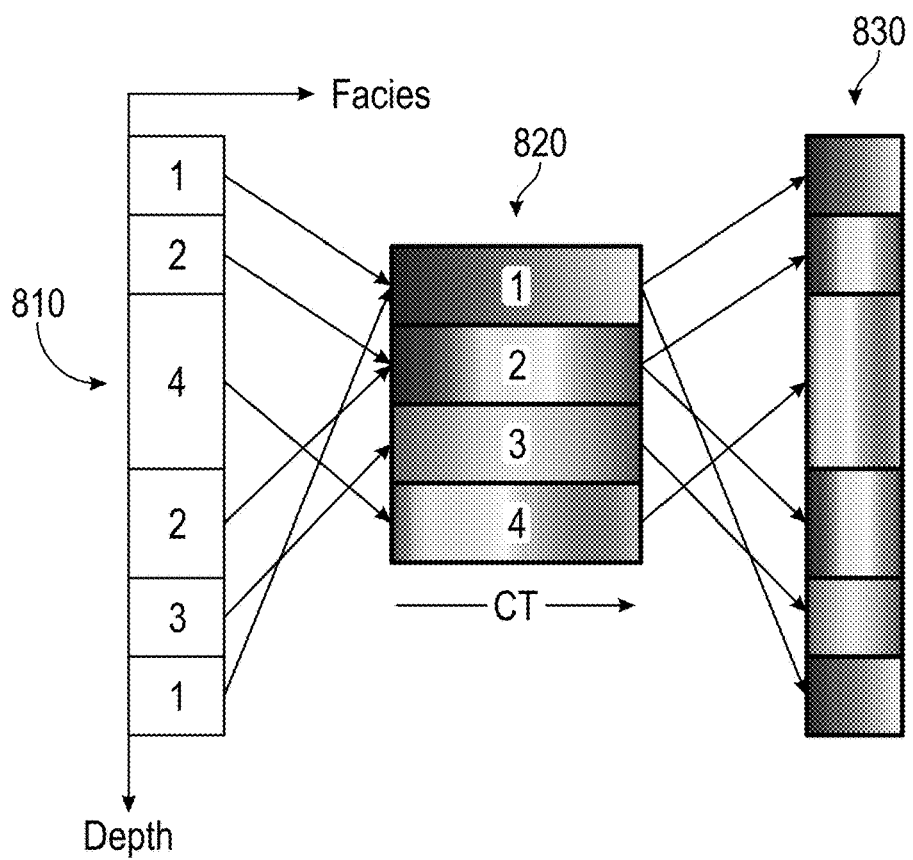
FIG. 8 is a chart showing a look up table transfer function modulation for a categorical formation property, according to various aspects of the present disclosure.

FIG. 8 is a chart showing a look up table transfer function modulation for a categorical formation property. As shown, image 810 illustrates a formation sample divided into multiple areas characterized by different values of a single categorical property. For example, if the categorical property being evaluated is facies, column 810 illustrates that four different types of facies were present in the formation sample, 1, 2, 3, and 4. Each facie integer can then be used as an index into a lookup table containing four different transfer functions, such as those shown in table 820 of FIG. 8. Accordingly, the arrows from column 810 to the table 820 illustrate selection of a transfer function. The transfer functions illustrated in table 820 are traditional transfer functions, mapping the image property value (CT value in this example) to a particular color and transparency combination. Although FIG. 8 is limited to presentation in black and white, according to the present disclosure, the column 810 and the table 820 are in color. For instance, in FIG. 8, in segment 1, the color ranges approximately from dark purple on the left side to yellow to green in the middle to yellow on the right side (represented by the darker black and white shades on the left of the figure to the lighter black and white shades on the right side), in segment 2, from dark blue on the left side, to green and yellow in the middle to red on the right side of the figure (represented by the darker black and white shades on the left and right sides of the figure with the lighter black and white shades in the middle), in segment 3 ranging from light blue on the left side of the figure to light red on the right side (represented by the degree in black and white shades across the segment from left to right of the figure), and in segment 4, ranging from dark blue to yellow in the middle to red and purple on the right (represented by the lighter black and white shades on the left side to the darker shades on the right of the figure). While FIG. 8 illustrates a transfer functions as a color transfer functions, it should be readily recognized by those having skill in the art that any suitable transfer function could be used including, but not limited to, grayscale, or any other transfer function suitable for indicating a difference in material. Next, the different values of categorical properties can be illustrated using the transfer function determined via the look-up table, as shown in graphical representation 830 of FIG. 8. Specifically, graphical representation 830 illustrates the color transfer function for each section of the formation sample as they are distributed throughout the sample.

Figure 9A:
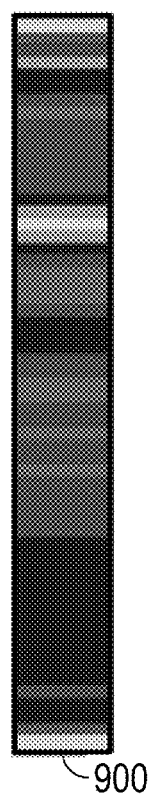
FIG. 9A is a graphical rendering illustrating an example distribution of a categorical log property values along a formation sample, according to various aspects of the present disclosure.
Figure 9B:
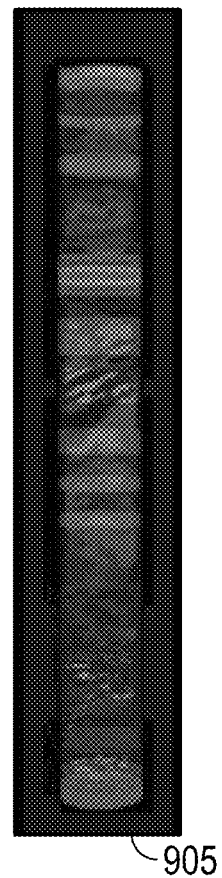
FIG. 9B depicts a graphical rendering which illustrates a graphical representation simultaneously showing an image of a formation sample modified with categorical color transfer function modulation; according to various aspects of the present disclosure

FIG. 9A is a graphical rendering 900 illustrating an example distribution of categorical log property values throughout a formation sample, each different categorical value illustrated using a different color. These may be obtained similarly to the lookup table in FIG. 9A, where each property is assigned an integer value, which corresponds to a color. FIG. 9B depicts a graphical rendering 905 which illustrates a graphical representation simultaneously showing an image of a formation sample modified with categorical color transfer function modulation. A user may therefore upon viewing the color simultaneously perceive the value of the property, such as the type of facies, and the texture or other visual characteristic of the image. In this manner, a user need not shift focus between a rendered image of a formation sample on one hand and a formation property graph on the other, but may simultaneously view a graphical representation of an image showing formation properties. However, there may be multiple other ways of modulating the transfer function parameters with the values of formation log property.

Based on the joint graphical representation of the image and the log property based on the transfer function, operators can make more informed decisions regarding a wellsite and carrying out wellbore operations. For instance, with more knowledge of the formation image and the associated properties, wellbore operations may be adjusted including, drilling operations including drilling rates and direction, fracturing operations, stimulation operations, production operations, secondary operations, diversion operations, hydrocarbon reservoir locating operations, and the like.

Figure 10:
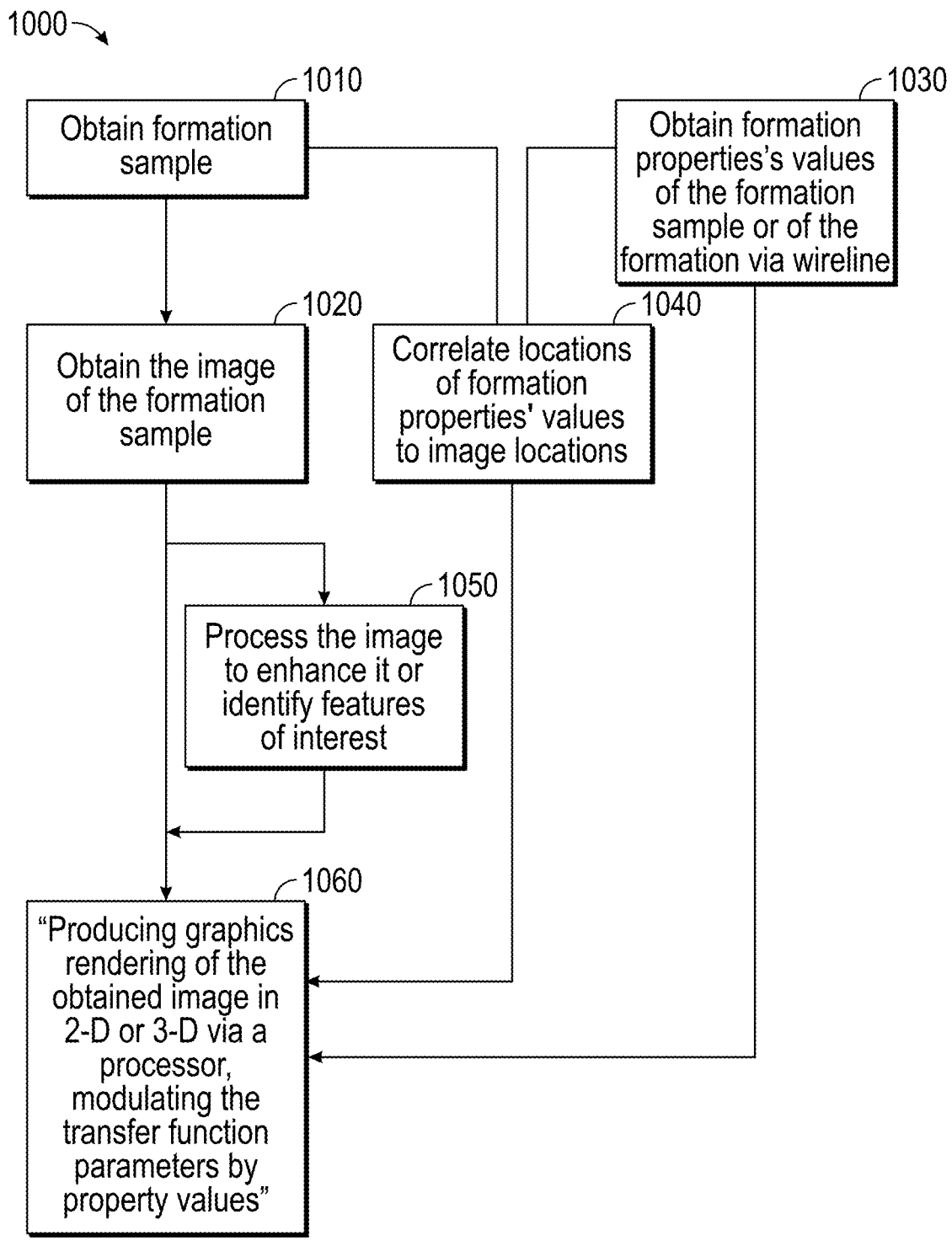
FIG. 10 is one implementation of the method according to some aspects of the present disclosure.

FIG. 10 is one implementation of the method 1000 according to some aspects of the present disclosure. In this implementation, the method may begin with step 1010, wherein a formation sample is acquired from well bore. The formation samples obtained from the well bore (step 1010) can include but are not limited to whole core, sidewall core, slabbed core, plugs acquired from core, cuttings, formation rock fragments, and the like. Next, in step 1020, an image of the formation sample is obtained or otherwise received. The imaging methods used in step 1020 can include, but are not limited to, a two-dimensional imaging (such as white-lite, UV-light, X-Ray projection, or thin section photography and the like), a three-dimensional imaging (such as a computerized tomography (CT), scanning electron microscopy (SEM)), or any other method suitable for obtaining a spatial distribution of a property within the sample. The resulting image can be a two-dimensional or three-dimensional image. The images so generated are presented in numerical form. After imaging is complete, the physical formation samples can be saved for further analysis or may be discarded. Alternatively, or additionally, the image of the formation can be taken from within the wellbore. The image may be optionally processed in step 1050 so as to enhance it or identify features of interest. In a parallel track, at step 1030 formation properties values may be obtained or otherwise received from the well bore, for example by logging, such as with a logging tool, such as acoustic logging, conductivity logging, NMR logging, gamma ray logging and the like. Each value of these properties is correlated to a location of the well bore, indicated by measured depth, and correlated in step 1040 to locations along the formation sample's dimension parallel to the well bore axis. As shown graphics rendering of the original image or processed image is created in step 1060. The transfer function used in creating the graphics rendering at each location of the image is modulated in step 1060 by values of one or more formation properties determined in step 1030 and correlated to the corresponding location of the image using correlation obtained in step 1040.

Figure 11:
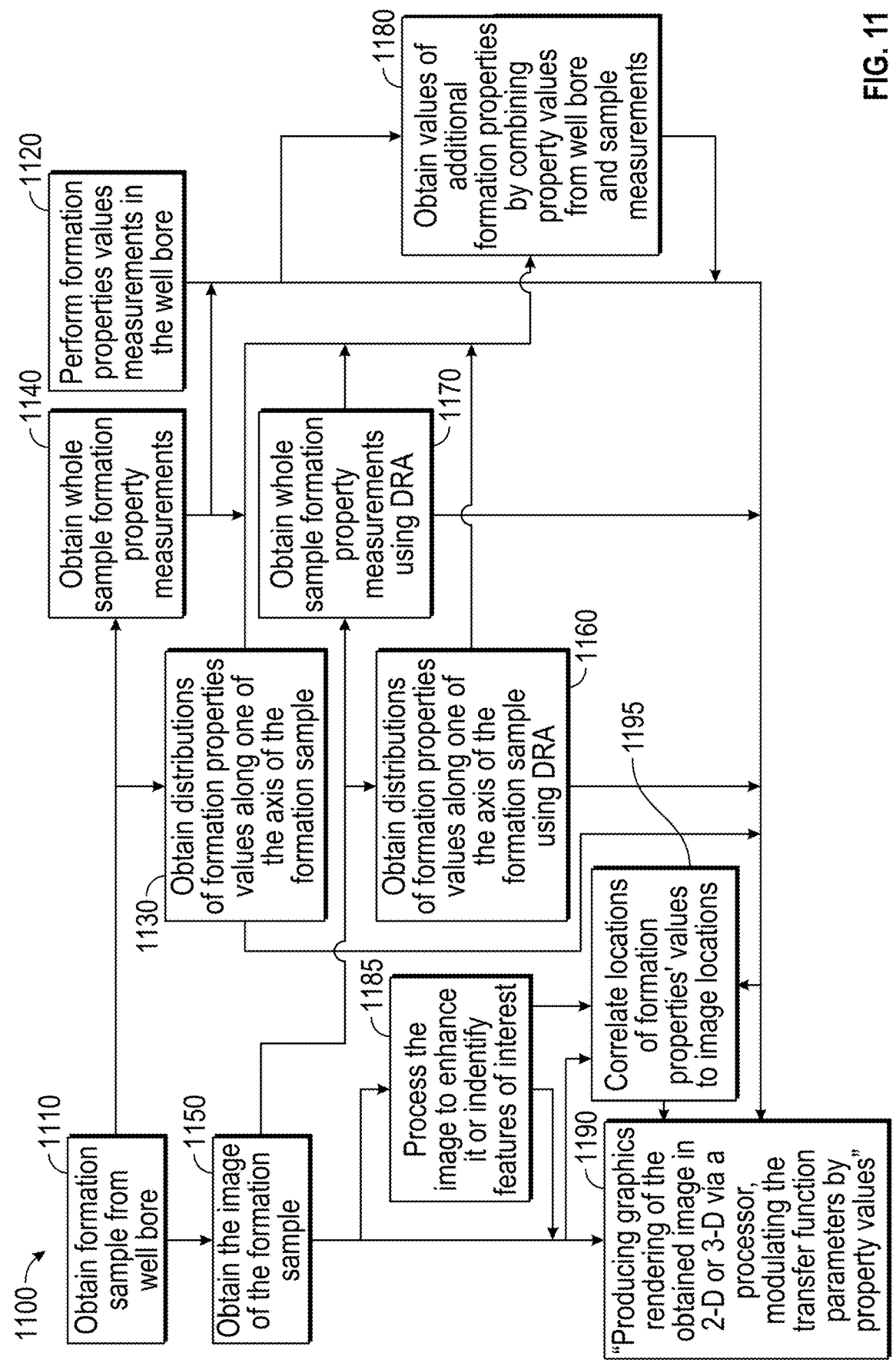
FIG. 11 is one implementation of the method according to some aspects of the present disclosure.

FIG. 11 is one implementation of the method 1100 according to some aspects of the present disclosure. In this implementation, in step 1110 a formation sample is acquired from well bore, and then as in in step 1150 an image of the formation sample may be obtained or otherwise received. In step 1185, the image may be processed to enhance or identify features of interest. The formation properties used to modulate the transfer function are obtained by measurements on the whole sample taken from the formation as in step 1140 or in multiple locations along the sample taken from the formation, as in step 1130. Alternatively, or additionally, the formation properties may be obtained or otherwise received by measurements performed in the wellbore as in step 1120. These formation properties may include but are not limited to density, total and spectral gamma ray intensity, elemental concentration, PE, acoustics, NMR measurements, and/or resistivity, among others.

The formation properties can also be obtained for the whole sample or in multiple locations along the sample from the image 1150 using methods of digital rock analysis, as in steps 1170 and 1160, respectively. The formation properties whose values are obtained from the formation sample image using digital rock analysis (DRA) methods in multiple locations along the formation sample and/or for the whole sample in steps 1160 and 1170 can include, but are not limited to, bulk density, PE, porosity, absolute permeability and other fluid flow characteristics, acoustic properties, geo-mechanical properties, grain and pore size distributions, rock types, formation types, etc. Any of the formation property values from the sample taken from the wellbore and properties measured from within the wellbore can be combined to obtain values of additional formation properties in step 1180. These property values obtained in step 1180 may include, but are not limited to, petrophysical properties, rock types, and similar. The aforementioned formation properties in method 1100 may have continuous or categorical values. As shown in step 1195 the locations at which log property values are obtained are correlated to locations in the image of the sample. As shown in step 1190 a graphics rendering of the 2-D or 3-D image or processed image is created. The transfer function used in creating the graphics rendering is modulated in step 1190 by values of one or more formation log properties, taken at the locations correlated in step 1195 to the locations of the image. The formation properties thus obtained are used to modulate the transfer function parameters used at the locations of the sample image where the property values are obtained, but any combination of formation properties from steps 1120, 1130, 1140, 1160, 1170 and 1180 can be used. In some implementations the formation property values can be encoded into the opacity and/or color of the graphics rendering of the sample image. In some implementations the formation property values can control which transfer functions are used for various parts of the image.

In one implementation correlation of the log property values locations to image location performed in step 1195 is performed by correlating measured depth values of the log properties and measured depth values of the sample image. In one implementation this correlation is performed by correlating the values of the coordinate along which the sample property distribution had been obtained with the coordinate of the sample image.

FIG. 12 illustrates a diagrammatic view of a conveyance logging wellbore operating environment 1200 (also referred to as "wireline" in the field) in which the present disclosure may be implemented. As depicted in FIG. 12, a hoist 1206 may be included as a portion of a platform 120, such as that coupled to derrick 125, and used with a conveyance 115 drawn from a spool 117 to raise or lower equipment such as tool 1210 into or out of a borehole. The tool 1210 may be a logging tool or an imaging tool to obtain imaging or log properties of wellbore 110. The tool 1210 may include for instance acoustic logging tools, electromagnetic logging tools, or other tools to obtain the log or image properties disclosed herein. A conveyance 1242 may provide a communicative coupling between the tool 1210 and a facility 1244 at the surface. The conveyance 1242 may include wires (one or more wires), slicklines, cables, or the like, as well as tubular conveyances such as coiled tubing, joint tubing, or other tubulars, and may include a downhole tractor. Additionally, power can be supplied via the conveyance 1242 to meet power requirements of the tool. The tool 1210 may have a local power supply, such as batteries, downhole generator and the like. When employing non-conductive cable, coiled tubing, pipe string, or downhole tractor, communication may be supported using, for example, wireless protocols (e.g. EM, acoustic, etc.), and/or measurements and logging data may be stored in local memory for subsequent retrieval. The facility 1244 may include a processing center 160 with one or more processors 161 capable of carrying out the methods and techniques of the present disclosure. In this manner, information about the formation 150 may be obtained by tool 1210 and processed by a computing device, such as processing center 160. In some embodiments, processing center 160 is equipped to process the received information in substantially real-time, while in some embodiments, processing center 160 can be equipped to store the received information for processing at some subsequent time.

Figure 13:
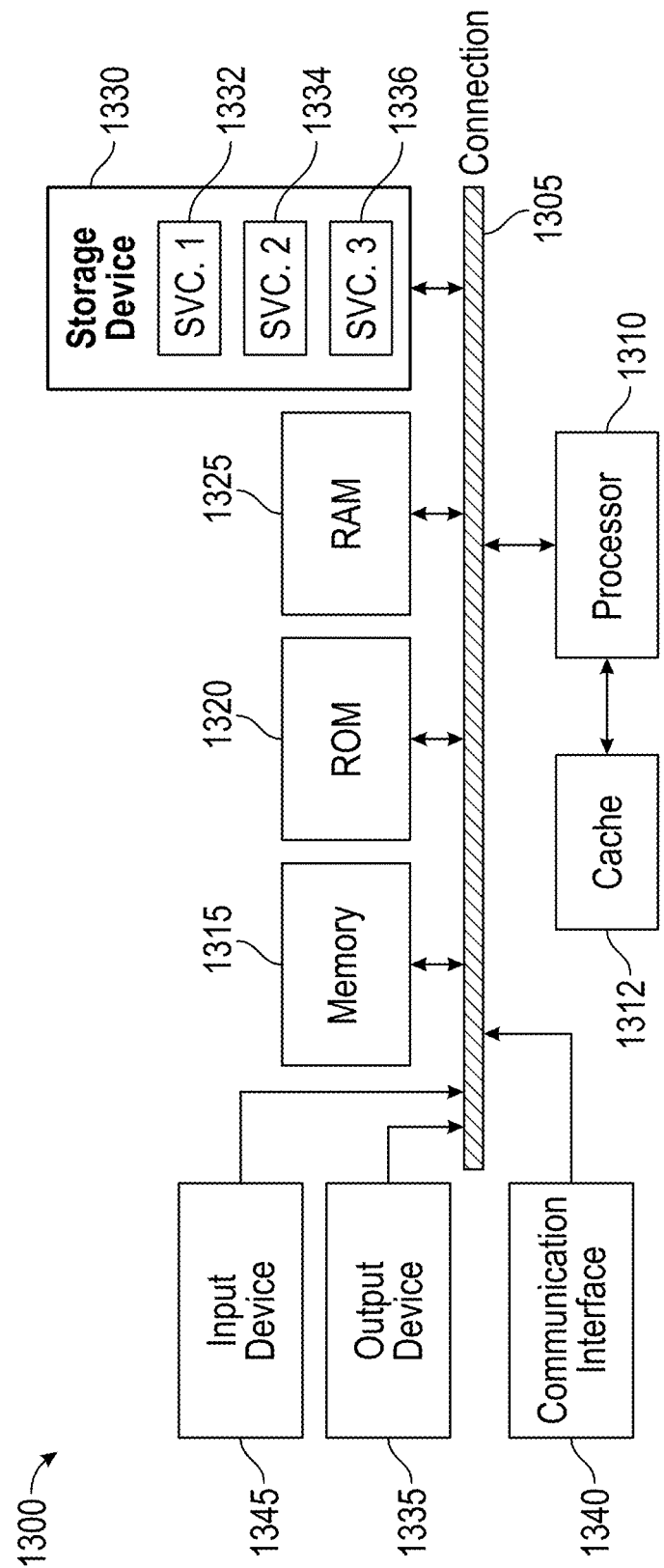
FIG. 13 illustrates an example computing device architecture which can be employed to perform various steps, methods, and techniques disclosed, in accordance with various aspects of the present disclosure.

The conveyance obtained imaging or logging as described in FIG. 12 may be in addition to or alternative to the formation sampling as described in FIGS. 1A and 1B. Accordingly, the image properties and log properties can be obtained via a formation sample as in FIGS. 1A and 1B and/or via conveyance logging and imaging of the wellbore. In some embodiments, the formation sample may be extracted from the wellbore as in FIGS. 1A and 1B and then imaged and/or its log properties obtained in a laboratory. Alternatively, or additionally, a formation sample may be extracted to FIGS. 1A and 1B and one of its log property or image obtained in a laboratory, and then the other of its log property or image property obtained from the wellbore. For instance if its log property is obtained of an extracted sample in a laboratory, then obtaining is imaging via conveyance as in FIG. 12, and alternatively, if its image property is obtained of an extracted sample in a laboratory then obtaining its log properties via conveyance as in FIG. 12. In such instances although the formation sample is extracted, the conveyance tool 1210 is used to obtain log properties or image properties from at or near where the formation sample was extracted via FIGS. 1A and 1B and such properties associated with the extracted formation sample. Further, the sampling apparatus of FIG. 1A can be carried out concurrently with other tools, such as conveyance tools of FIG. 12 to obtain formation samples while simultaneously obtained image or log properties. FIG. 13 illustrates an example computing device architecture 1400 which can be employed to perform various steps, methods, and techniques disclosed herein. Persons of ordinary skill in the art will also readily appreciate that other system implementations or examples are possible.

As noted above, FIG. 13 illustrates an example computing device architecture 1300 of a computing device which can implement the various technologies and techniques described herein. The computing device architecture 1300 can process the imaging of formation samples, or acquisition of formation properties, process and modify transfer function, and may graphically render the obtained images using a transfer function and/or modulate the transfer function to create a graphical representation of the image and/or the properties, and the simultaneous display of the image and/or the properties and graphically depict the image as if it were overlaid with formation properties on a computer screen or other canvas. The computing device architecture 1300 can be employed with one or more processors 161 of processing facility 160 in FIGS. 1A, 1B and 12. For example, the computing device architecture 1300 can implement the various training systems, detection systems, data processors, downhole tools, servers, or other computing devices and perform various steps, methods, and techniques disclosed herein. The components of the computing device architecture 1300 are shown in electrical communication with each other using a connection 1305, such as a bus. The example computing device architecture 1300 includes a processing unit (CPU or processor) 1310 and a computing device connection 1305 that couples various computing device components including the computing device memory 1315, such as read only memory (ROM) 1320 and random access memory (RAM) 1325, to the processor 1310.

The computing device architecture 1300 can include a cache of high-speed memory 1312 connected directly with, in close proximity to, or integrated as part of the processor 1310. The computing device architecture 1300 can copy data from the memory 1415 and/or the storage device 1330 to the cache 1312 for quick access by the processor 1310. In this way, the cache can provide a performance boost that avoids processor 1310 delays while waiting for data. These and other modules can control or be configured to control the processor 1310 to perform various actions. Other computing device memory 1315 may be available for use as well. The memory 1315 can include multiple different types of memory with different performance characteristics. The processor 1310 can include any general purpose processor and a hardware or software service, such as service 11332, service 21334, and service 31336 stored in storage device 1330, configured to control the processor 1310 as well as a special-purpose processor where software instructions are incorporated into the processor design. The processor 1310 may be a self-contained system, containing multiple cores or processors, a bus, memory controller, cache, etc. A multi-core processor may be symmetric or asymmetric.

To enable user interaction with the computing device architecture 1400, an input device 1345 can represent any number of input mechanisms, such as a microphone for speech, a touch-sensitive screen for gesture or graphical input, keyboard, mouse, motion input, speech and so forth. An output device 1335 can also be one or more of a number of output mechanisms known to those of skill in the art, such as a display, projector, television, speaker device, virtual reality goggles, etc. In some instances, multimodal computing devices can enable a user to provide multiple types of input to communicate with the computing device architecture 1300. The communications interface 1340 can generally govern and manage the user input and computing device output. There is no restriction on operating on any particular hardware arrangement and therefore the basic features here may easily be substituted for improved hardware or firmware arrangements as they are developed.

Storage device 1330 is a non-volatile memory and can be a hard disk or other types of computer readable media which can store data that are accessible by a computer, such as magnetic cassettes, flash memory cards, solid state memory devices, digital versatile disks, cartridges, random access memories (RAMs) 1325, read only memory (ROM) 1320, and hybrids thereof. The storage device 1330 can include services 1332, 1334, 1336 for controlling the processor 1310. Other hardware or software modules are contemplated. The storage device 1330 can be connected to the computing device connection 1305. In one aspect, a hardware module that performs a particular function can include the software component stored in a computer-readable medium in connection with the necessary hardware components, such as the processor 1310, connection 1305, output device 1335, and so forth, to carry out the function.

For clarity of explanation, in some instances the present technology may be presented as including individual functional blocks including functional blocks comprising devices, device components, steps or routines in a method embodied in software, or combinations of hardware and software.

In some embodiments the computer-readable storage devices, mediums, and memories can include a cable or wireless signal containing a bit stream and the like. However, when mentioned, non-transitory computer-readable storage media expressly exclude media such as energy, carrier signals, electromagnetic waves, and signals per se.

Methods according to the above-described examples can be implemented using computer-executable instructions that are stored or otherwise available from computer readable media. Such instructions can include, for example, instructions and data which cause or otherwise configure a general purpose computer, special purpose computer, or a processing device to perform a certain function or group of functions. Portions of computer resources used can be accessible over a network. The computer executable instructions may be, for example, binaries, intermediate format instructions such as assembly language, firmware, source code, etc. Examples of computer-readable media that may be used to store instructions, information used, and/or information created during methods according to described examples include magnetic or optical disks, flash memory, USB devices provided with non-volatile memory, networked storage devices, and so on.

Devices implementing methods according to these disclosures can include hardware, firmware and/or software, and can take any of a variety of form factors. Typical examples of such form factors include laptops, smart phones, small form factor personal computers, personal digital assistants, rackmount devices, standalone devices, and so on. Functionality described herein also can be embodied in peripherals or add-in cards. Such functionality can also be implemented on a circuit board among different chips or different processes executing in a single device, by way of further example.

The instructions, media for conveying such instructions, computing resources for executing them, and other structures for supporting such computing resources are example means for providing the functions described in the disclosure.

In the foregoing description, aspects of the application are described with reference to specific embodiments thereof, but those skilled in the art will recognize that the application is not limited thereto. Thus, while illustrative embodiments of the application have been described in detail herein, it is to be understood that the disclosed concepts may be otherwise variously embodied and employed, and that the appended claims are intended to be construed to include such variations, except as limited by the prior art. Various features and aspects of the above-described subject matter may be used individually or jointly. Further, embodiments can be utilized in any number of environments and applications beyond those described herein without departing from the broader spirit and scope of the specification. The specification and drawings are, accordingly, to be regarded as illustrative rather than restrictive. For the purposes of illustration, methods were described in a particular order. It should be appreciated that in alternate embodiments, the methods may be performed in a different order than that described.

Where components are described as being "configured to" perform certain operations, such configuration can be accomplished, for example, by designing electronic circuits or other hardware to perform the operation, by programming programmable electronic circuits (e.g., microprocessors, or other suitable electronic circuits) to perform the operation, or any combination thereof.

The various illustrative logical blocks, modules, circuits, and algorithm steps described in connection with the examples disclosed herein may be implemented as electronic hardware, computer software, firmware, or combinations thereof. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present application.

The techniques described herein may also be implemented in electronic hardware, computer software, firmware, or any combination thereof. Such techniques may be implemented in any of a variety of devices such as general purposes computers, wireless communication device handsets, or integrated circuit devices having multiple uses including application in wireless communication device handsets and other devices. Any features described as modules or components may be implemented together in an integrated logic device or separately as discrete but interoperable logic devices. If implemented in software, the techniques may be realized at least in part by a computer-readable data storage medium comprising program code including instructions that, when executed, performs one or more of the method, algorithms, and/or operations described above. The computer-readable data storage medium may form part of a computer program product, which may include packaging materials.

The computer-readable medium may include memory or data storage media, such as random access memory (RAM) such as synchronous dynamic random access memory (SDRAM), read-only memory (ROM), non-volatile random access memory (NVRAM), electrically erasable programmable read-only memory (EEPROM), FLASH memory, magnetic or optical data storage media, and the like. The techniques additionally, or alternatively, may be realized at least in part by a computer-readable communication medium that carries or communicates program code in the form of instructions or data structures and that can be accessed, read, and/or executed by a computer, such as propagated signals or waves.

Other embodiments of the disclosure may be practiced in network computing environments with many types of computer system configurations, including personal computers, hand-held devices, multi-processor systems, microprocessor-based or programmable consumer electronics, network PCs, minicomputers, mainframe computers, and the like. Embodiments may also be practiced in distributed computing environments where tasks are performed by local and remote processing devices that are linked (either by hard-wired links, wireless links, or by a combination thereof) through a communications network. In a distributed computing environment, program modules may be located in both local and remote memory storage devices.

Numerous examples are provided herein to enhance understanding of the present disclosure. A specific set of statements are provided as follows.

Statement 1: A method including: receiving an image of a formation, the image comprising image values based on the formation; receiving a log property of the formation, the log property comprising log property values based on the formation; correlating locations of the log property values of the formation to corresponding locations in the image; determining a transfer function with the image values and the correlated log property values as inputs; rendering a joint graphical representation of the image and the log property based on the transfer function; and visualizing the joint graphical representation on a screen.

Statement 2: The method of Statement 1, further including, taking an image of a sample extracted from a downhole formation to obtain the image of the formation. Statement 3: The method of any one of the preceding Statements 1-2, wherein the image of the formation is obtained from within a wellbore. Statement 4: The method of any one of the preceding Statements 1-3, wherein the log property of the formation is measured on a sample extracted from a downhole formation. Statement 5: The method of any one of the preceding Statements 1-4, the log property of the formation is measured from within a wellbore. Statement 6: The method of any one of the preceding Statements 1-5, wherein the graphical representation comprises a representation of the image of the formation appearing combined with a representation of the log property across a surface area of the image. Statement 7: The method of any one of the preceding Statements 1-6, wherein the transfer function comprises relating the image to a graphical element and a location of the graphical element in the graphical representation. Statement 8: The method of any one of the preceding Statements 1-7, further including mapping the image values via a look up table having the image value matched to components of the transfer function. Statement 9: The method of any one of the preceding Statements 1-8, wherein the transfer function may be represented as:

$$F_i[v(x_1,x_2,x_3),u(y)]$$

wherein
i enumerates components of a color space and optionally opacity,
v is a value of the formation image at a location with coordinates $(x_1,x_2,x_3)$,
u is the value of the log property at the location with coordinate y associated with the location $(x_1,x_2,x_3)$ of the image.

Statement 10: The method of any one of the preceding Statements 1-9, wherein the rendering comprises defining the components of elements of graphical representation. Statement 11: The method of any one of the preceding Statements 1-10, wherein components of the transfer function comprise opacity and/or color. Statement 12: The method of any one of the preceding Statements 1-11, the image is a two-dimensional image. Statement 13: The method of any one of the preceding Statements 1-12, wherein the two dimensional image is acquired via one or more members selected from the group of white-lite, UV-light, X-Ray projection, acoustic, resistivity or thin section photography. Statement 14: The method of any one of the preceding Statements 1-13, wherein the image is a three-dimensional image. Statement 15: The method of any one of the preceding Statements 1-14, wherein the three-dimensional image is acquired via one or more members selected from computerized tomography (CT), scanning electron microscopy (SEM), and magnetic resonance imaging (MRI).

Statement 16: The method of any one of the preceding Statements 1-15, wherein the log property comprises one or more selected from the group of weight fractions of chemical elements, X-ray fluorescence (XRF), spectral gamma ray counts, mineral composition using X-ray diffraction (XRD), porosity, absolute and relative permeability, density, pore and pore throat size distributions, bulk density, porosity, photoelectric effect (PE), fluid saturation and composition, elastic and geo-mechanical properties, rock types, and formation types.

Statement 17: A system including: one or more processors; and at least one non-transitory computer-readable storage medium storing instructions which, when executed by the one or more processors, cause the system to: receiving an image of a formation, the image comprising image values based on the formation; receiving a log property of the formation, the log property comprising property values based on the formation; correlating locations of the log property values of the formation to corresponding locations in the image; determining a transfer function with the image values and the correlated log property values as inputs; rendering a joint graphical representation of the image and the log property based on the transfer function; and visualizing the joint graphical representation on a screen.

Statement 18: The system of Statement 17, wherein the transfer function may be represented as:

$$F_i[v(x_1,x_2,x_3),u(y)]$$

wherein i enumerates components of a color space and optionally opacity, is a value of formation property image at a location with coordinates $(x_1,x_2,x_3)$, u is the value of the formation property at the location with coordinate y associated with the location $(x_1,x_2,x_3)$ of the image.

Statement 19: A non-transitory computer readable storage medium storing computer-executable instructions which, when executed by one or more processors, cause the one or more processors to: receive an image of a formation, the image comprising image values based on the formation; receive a log property of the formation, the log property comprising property values based on the formation; correlate locations of the log property values of the formation to corresponding locations in the image; determine a transfer function with the image values and the correlated log property values as inputs; and visualizing the joint graphical representation on a screen. Statement 20: The non-transitory computer readable storage medium of Statement 19, wherein the transfer function may be represented as:

$$F_i[v(x_1,x_2,x_3),u(y)]$$

wherein i enumerates components of a color space and optionally opacity, is a value of formation property image at a location with coordinates $(x_1,x_2,x_3)$, u is the value of the formation property at the location with coordinate y associated with the location $(x_1,x_2,x_3)$ of the image.

What is claimed is:

1. A method comprising:
    receiving an image of a formation, the image comprising image values based on the formation;
    receiving a log property of the formation, the log property comprising log property values based on the formation;
    correlating locations of the log property values of the formation to corresponding locations in the image;
    determining a transfer function with the image values and the correlated log property values as inputs;
    wherein the transfer function is represented as:

$$F_i[v(x_1,x_2,x_3),u(y)]$$

wherein
    i enumerates components of a color space and optionally opacity,
    v is a value of the formation image at a location with coordinates $(x_1,x_2,x_3)$,
    u is the value of the log property at the location with coordinate y associated with the locations $(x_1,x_2,x_3)$ of the image;
    rendering a joint graphical representation of the image and the log property based on the transfer function; and
    visualizing the joint graphical representation on a screen.

2. The method of claim 1, further comprising, taking an image of a sample extracted from a downhole formation to obtain the image of the formation.

3. The method of claim 1, wherein the image of the formation is obtained from within a wellbore.

4. The method of claim 1, wherein the log property of the formation is measured on a sample extracted from a downhole formation.

5. The method of claim 1, wherein the log property of the formation is measured from within a wellbore.

6. The method of claim 1, wherein the graphical representation comprises a representation of the image of the formation appearing combined with a representation of the log property across a surface area of the image.

7. The method of claim 1, wherein the transfer function comprises relating the image to a graphical element and a location of the graphical element in the graphical representation.

8. The method of claim 1, further comprising mapping the image values via a look up table having the image value matched to components of the transfer function.

9. The method of claim 1, wherein the rendering comprises defining the components of elements of graphical representation.

10. The method of claim 1, wherein components of the transfer function comprise opacity and/or color.

11. The method of any one of claims 1 to 3, wherein the image is a two-dimensional image.

12. The method of claim 11, wherein the two dimensional image is acquired via one or more members selected from the group of white-lite, UV-light, X-Ray projection, acoustic, resistivity or thin section photography.

13. The method of any one of claims 1 to 3, wherein the image is a three-dimensional image.

14. The method of claim 13, wherein the three-dimensional image is acquired via one or more members selected from computerized tomography (CT), scanning electron microscopy (SEM), and magnetic resonance imaging (MRI).

15. The method of any one of claim 1, 4, or 5, wherein the log property comprises one or more selected from the group of weight fractions of chemical elements, X-ray fluorescence (XRF), spectral gamma ray counts, mineral composition using X-ray diffraction (XRD), porosity, absolute and relative permeability, density, pore and pore throat size distributions, bulk density, porosity, photoelectric effect (PE), mineral fractions distribution, fluid saturation and composition, permeability and other fluid flow characteristics, mineral composition, elastic and geo-mechanical properties, rock types, and formation types.

16. A system comprising:
    one or more processors; and
    at least one non-transitory computer-readable storage medium storing instructions which, when executed by the one or more processors, cause the system to:
    receiving an image of a formation, the image comprising image values based on the formation;
    receiving a log property of the formation, the log property comprising property values based on the formation;
    correlating locations of the log property values of the formation to corresponding locations in the image;
    determining a transfer function with the image values and the correlated log property values as inputs;
    wherein the transfer function is represented as:

$$F_i[v(x_1,x_2,x_3),u(y)]$$

wherein
    i enumerates components of a color space and optionally opacity,
    v is a value of the formation image at a location with coordinates $(x_1,x_2,x_3)$, u is the value of the log property at the location with coordinate y associated with the location $(x_1,x_2,x_3)$ of the image;

rendering a joint graphical representation of the image and the log property based on the transfer function; and visualizing the joint graphical representation on a screen.

17. A non-transitory computer readable storage medium storing computer-executable instructions which, when executed by one or more processors, cause the one or more processors to:

receive an image of a formation, the image comprising image values based on the formation;

receive a log property of the formation, the log property comprising property values based on the formation;

correlate locations of the log property values of the formation to corresponding locations in the image;

determine a transfer function with the image values and the correlated log property values as inputs; and wherein the transfer function is represented as:

$$F_i[v(x_1,x_2,x_3),u(y)]$$

wherein
- i enumerates components of a color space and optionally opacity,
- v is a value of the formation image at a location with coordinates $(x_1,x_2,x_3)$,
- u is the value of the log property at the location with coordinate y associated with the location $(x_1,x_2,x_3)$ of the image;

visualizing the joint graphical representation on a screen.

* * * * *